(12) United States Patent
Denenburg

(10) Patent No.: US 12,274,670 B2
(45) Date of Patent: Apr. 15, 2025

(54) LIQUID TRANSFER DEVICE WITH INTEGRATED SYRINGE

(71) Applicant: WEST PHARMA. SERVICES IL, LTD., Ra'anana (IL)

(72) Inventor: Igor Denenburg, Gedera (IL)

(73) Assignee: WEST PHARMA. SERVICES IL, ltd., Ra'anana (IL)

( * ) Notice: Subject to any disclaimer, the term of this patent is extended or adjusted under 35 U.S.C. 154(b) by 299 days.

(21) Appl. No.: 17/767,906

(22) PCT Filed: Mar. 26, 2020

(86) PCT No.: PCT/IL2020/050362
§ 371 (c)(1),
(2) Date: Apr. 10, 2022

(87) PCT Pub. No.: WO2020/208626
PCT Pub. Date: Oct. 15, 2020

(65) Prior Publication Data
US 2024/0099936 A1    Mar. 28, 2024

Related U.S. Application Data

(60) Provisional application No. 62/831,214, filed on Apr. 9, 2019.

(51) Int. Cl.
*A61J 1/20* (2006.01)
*A61J 1/10* (2006.01)

(52) U.S. Cl.
CPC .............. *A61J 1/10* (2013.01); *A61J 1/2013* (2015.05); *A61J 1/2055* (2015.05); *A61J 1/2062* (2015.05); *A61J 1/2096* (2013.01)

(58) Field of Classification Search
CPC ...... A61J 1/2058; A61J 1/2037; A61J 1/2062; A61J 1/2055; A61J 1/2089; A61J 1/2051;
(Continued)

(56) References Cited

U.S. PATENT DOCUMENTS

| 62,333 A | 2/1867 | Hall |
| 247,975 A | 10/1881 | Wickes |

(Continued)

FOREIGN PATENT DOCUMENTS

| CA | 2946559 A1 | 10/2015 |
| CN | 1636605 A | 7/2005 |

(Continued)

OTHER PUBLICATIONS

U.S. Appl. No. 14/385,212 by Lev, filed Sep. 15, 2014.
(Continued)

*Primary Examiner* — Sarah Al Hashimi
*Assistant Examiner* — Arjuna P Chatrathi
(74) *Attorney, Agent, or Firm* — Blank Rome LLP

(57) ABSTRACT

A liquid transfer device is provided for mixing a medicament additive contained within a vial with an infusion liquid contained within an infusion liquid container to form a medicated infusion liquid. The liquid transfer device includes a trifurcated connector body defining a barrel at a first end thereof, an IV spike at a second end thereof and a vial adapter lumen with a vial adapter secured thereto at a third end thereof. A plunger having an IV port is slidably engaged with the barrel to form a syringe integrated with the device. The syringe enables the device to flush out the flow path between the IV port and the IV spike connected to the medicated infusion liquid, and any residual unmixed medicament additive therein, after combining the medicament additive with the infusion liquid.

20 Claims, 15 Drawing Sheets

(58) Field of Classification Search
CPC .... A61J 3/002; A61M 5/1407; A61M 5/1408; A61M 5/1409; A61M 5/162; A61M 5/31596; A61M 2005/31598; A61M 5/31531; A61M 5/31513; A61M 5/31515; A61M 2005/31516; A61M 2005/31521; A61M 2005/31523

See application file for complete search history.

(56) References Cited

U.S. PATENT DOCUMENTS

| | | | |
|---|---|---|---|
| 254,444 A | 2/1882 | Vogel et al. | |
| 300,060 A | 6/1884 | Ford | |
| 1,021,681 A | 3/1912 | Jennings | |
| 1,704,817 A | 3/1929 | Ayers | |
| 1,930,944 A | 10/1933 | Schmitz, Jr. | |
| 2,326,490 A | 8/1943 | Perelson | |
| 2,560,162 A | 7/1951 | Ferguson | |
| 2,748,769 A | 6/1956 | Jennie | |
| 2,830,587 A | 4/1958 | James | |
| 2,931,668 A | 4/1960 | Baley | |
| 2,968,497 A | 1/1961 | Mervyn | |
| 3,059,643 A | 10/1962 | Barton | |
| D198,499 S | 6/1964 | Andrew et al. | |
| 3,225,763 A | 12/1965 | Waterman | |
| 3,277,893 A | 10/1966 | Clark | |
| 3,306,502 A * | 2/1967 | Harris, Jr. | G01N 30/18 604/218 |
| 3,308,822 A | 3/1967 | De Luca | |
| 3,484,849 A | 12/1969 | Huebner et al. | |
| 3,618,637 A | 11/1971 | Santomieri | |
| 3,757,981 A | 9/1973 | Harris, Sr. et al. | |
| D229,518 S | 12/1973 | Albert | |
| 3,782,365 A | 1/1974 | Pinna | |
| 3,788,524 A | 1/1974 | Davis et al. | |
| 3,822,700 A | 7/1974 | Pennington | |
| 3,826,261 A | 7/1974 | Killinger | |
| 3,872,992 A | 3/1975 | Larson | |
| 3,885,607 A | 5/1975 | Peltier | |
| 3,938,520 A | 2/1976 | Scislowicz et al. | |
| 3,957,052 A | 5/1976 | Topham | |
| 3,977,555 A | 8/1976 | Larson | |
| 3,993,063 A | 11/1976 | Larrabee | |
| 4,020,839 A | 5/1977 | Klapp | |
| 4,026,128 A | 5/1977 | Blanco | |
| 4,051,852 A | 10/1977 | Villari | |
| D247,975 S | 5/1978 | Luther | |
| D248,568 S | 7/1978 | Smach | |
| 4,109,670 A | 8/1978 | Slagel | |
| 4,121,585 A | 10/1978 | Becker, Jr. | |
| 4,161,178 A | 7/1979 | Genese | |
| 4,187,848 A | 2/1980 | Taylor | |
| D254,444 S | 3/1980 | Levine | |
| 4,203,067 A | 5/1980 | Bollongino et al. | |
| 4,203,443 A | 5/1980 | Genese | |
| 4,210,173 A | 7/1980 | Choksi et al. | |
| D257,286 S | 10/1980 | Folkman | |
| 4,253,501 A | 3/1981 | Ogle | |
| 4,262,671 A | 4/1981 | Kersten | |
| 4,296,786 A | 10/1981 | Brignola | |
| 4,303,067 A | 12/1981 | Connolly et al. | |
| 4,312,349 A | 1/1982 | Cohen | |
| 4,314,586 A | 2/1982 | Folkman | |
| 4,323,066 A * | 4/1982 | Bourdon | A61M 5/2053 604/228 |
| 4,328,802 A | 5/1982 | Curley et al. | |
| 4,335,717 A | 6/1982 | Bujan et al. | |
| D267,199 S | 12/1982 | Koenig | |
| 4,364,387 A | 12/1982 | Larkin | |
| 4,376,634 A | 3/1983 | Prior et al. | |
| D268,871 S | 5/1983 | Benham et al. | |
| 4,392,850 A | 7/1983 | Elias et al. | |
| D270,282 S | 8/1983 | Gross | |
| 4,410,321 A | 10/1983 | Pearson et al. | |
| 4,411,662 A | 10/1983 | Pearson | |
| D271,421 S | 11/1983 | Fetterman | |
| 4,434,823 A | 3/1984 | Hudspith | |
| 4,465,471 A | 8/1984 | Harris et al. | |
| 4,475,915 A | 10/1984 | Sloane | |
| 4,493,348 A | 1/1985 | Lemmons | |
| 4,505,709 A | 3/1985 | Froning et al. | |
| 4,507,113 A | 3/1985 | Dunlap | |
| D280,018 S | 8/1985 | Scott | |
| 4,532,969 A | 8/1985 | Kwaan | |
| 4,534,758 A | 8/1985 | Akers et al. | |
| 4,561,445 A | 12/1985 | Berke et al. | |
| 4,564,054 A | 1/1986 | Gustavsson | |
| 4,573,993 A | 3/1986 | Hoag et al. | |
| 4,576,211 A | 3/1986 | Valentini et al. | |
| 4,581,014 A | 4/1986 | Millerd et al. | |
| 4,585,446 A | 4/1986 | Kempf | |
| 4,588,396 A | 5/1986 | Stroebel et al. | |
| 4,588,403 A | 5/1986 | Weiss et al. | |
| D284,603 S | 7/1986 | Oignon | |
| 4,604,093 A | 8/1986 | Brown et al. | |
| 4,607,671 A | 8/1986 | Aalto et al. | |
| 4,614,437 A | 9/1986 | Buehler | |
| 4,638,975 A | 1/1987 | Iuchi et al. | |
| 4,639,019 A | 1/1987 | Mittleman | |
| 4,667,927 A | 5/1987 | Oscarsson | |
| 4,675,020 A | 6/1987 | Mcphee | |
| 4,676,530 A | 6/1987 | Nordgren et al. | |
| D291,490 S | 8/1987 | Raines | |
| 4,683,975 A | 8/1987 | Booth et al. | |
| 4,697,622 A | 10/1987 | Swift et al. | |
| 4,721,133 A | 1/1988 | Sundblom | |
| 4,729,401 A | 3/1988 | Raines | |
| 4,735,608 A | 4/1988 | Sardam | |
| 4,743,229 A | 5/1988 | Chu | |
| 4,743,243 A | 5/1988 | Vaillancourt | |
| 4,752,292 A | 6/1988 | Lopez et al. | |
| 4,758,235 A | 7/1988 | Tu | |
| 4,759,756 A | 7/1988 | Forman et al. | |
| 4,778,447 A | 10/1988 | Velde et al. | |
| 4,787,898 A | 11/1988 | Raines | |
| 4,797,898 A | 1/1989 | Martinez | |
| D300,060 S | 2/1989 | Molgaard-Nielsen | |
| 4,804,366 A | 2/1989 | Zdeb et al. | |
| 4,826,492 A | 5/1989 | Magasi | |
| 4,832,690 A | 5/1989 | Kuu | |
| 4,834,152 A | 5/1989 | Howson et al. | |
| 4,834,744 A | 5/1989 | Ritson | |
| D303,013 S | 8/1989 | Konopka | |
| 4,857,062 A | 8/1989 | Russell | |
| 4,865,592 A | 9/1989 | Rycroft | |
| 4,871,463 A | 10/1989 | Taylor et al. | |
| 4,898,209 A | 2/1990 | Zdeb | |
| 4,909,290 A | 3/1990 | Coccia | |
| 4,919,596 A | 4/1990 | Slate et al. | |
| 4,927,423 A | 5/1990 | Malmborg | |
| 4,931,040 A | 6/1990 | Haber et al. | |
| 4,932,944 A | 6/1990 | Jagger et al. | |
| 4,967,797 A | 11/1990 | Manska | |
| D314,050 S | 1/1991 | Sone | |
| D314,622 S | 2/1991 | Andersson et al. | |
| 4,997,430 A | 3/1991 | Van Der Heiden et al. | |
| 5,006,114 A | 4/1991 | Rogers et al. | |
| 5,035,686 A | 7/1991 | Crittenden et al. | |
| 5,041,105 A | 8/1991 | D'Alo et al. | |
| 5,045,066 A | 9/1991 | Scheuble et al. | |
| 5,049,129 A | 9/1991 | Zdeb et al. | |
| 5,053,015 A | 10/1991 | Gross | |
| 5,061,248 A | 10/1991 | Sacco | |
| 5,088,996 A | 2/1992 | Kopfer et al. | |
| 5,096,575 A | 3/1992 | Cosack | |
| 5,104,387 A | 4/1992 | Pokorney et al. | |
| 5,113,904 A | 5/1992 | Aslanian | |
| 5,122,124 A | 6/1992 | Novacek et al. | |
| 5,125,908 A | 6/1992 | Cohen | |
| 5,125,915 A | 6/1992 | Berry et al. | |
| D328,788 S | 8/1992 | Sagae et al. | |
| D331,281 S | 11/1992 | Levine | |
| 5,171,230 A | 12/1992 | Eland et al. | |
| 5,181,508 A | 1/1993 | Poole, Jr. | |

(56) References Cited

U.S. PATENT DOCUMENTS

| | | |
|---|---|---|
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| D337,828 S | 7/1993 | David |
| 5,232,029 A | 8/1993 | Knox et al. |
| 5,232,109 A | 8/1993 | Tirrell et al. |
| 5,242,432 A | 9/1993 | Defrank |
| 5,247,972 A | 9/1993 | Tetreault |
| D341,420 S | 11/1993 | Conn |
| 5,269,768 A | 12/1993 | Cheung |
| 5,270,219 A | 12/1993 | Decastro et al. |
| 5,279,576 A | 1/1994 | Loo et al. |
| 5,288,290 A | 2/1994 | Brody |
| 5,300,034 A | 4/1994 | Behnke et al. |
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | Mcphee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Oesterlind et al. |
| 5,674,195 A | 10/1997 | Truthan |
| 5,676,346 A | 10/1997 | Einsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial, Jr. |
| D393,722 S | 4/1998 | Fangrow et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Mueller |
| 5,806,831 A | 9/1998 | Paradis |
| 5,810,792 A | 9/1998 | Fangrow et al. |
| 5,814,020 A | 9/1998 | Gross |
| D399,558 S | 10/1998 | Guala et al. |
| D399,559 S | 10/1998 | Molina |
| 5,817,082 A | 10/1998 | Niedospial et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| D403,398 S | 12/1998 | Guala et al. |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |
| D414,562 S | 9/1999 | Tajima |
| 5,954,104 A | 9/1999 | Daubert et al. |
| 5,968,022 A | 10/1999 | Saito |
| 5,971,181 A | 10/1999 | Niedospial et al. |
| 5,971,965 A | 10/1999 | Mayer |
| D416,086 S | 11/1999 | Parris et al. |
| 5,989,237 A | 11/1999 | Fowles et al. |
| D417,733 S | 12/1999 | Howell et al. |
| 6,003,566 A | 12/1999 | Thibault et al. |

(56) References Cited

U.S. PATENT DOCUMENTS

| | | |
|---|---|---|
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote et al. |
| D422,357 S | 4/2000 | Niedospial et al. |
| 6,053,899 A | 4/2000 | Slanda et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A | 10/2000 | Niedospial et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial et al. |
| 6,159,192 A | 12/2000 | Fowles et al. |
| 6,162,199 A | 12/2000 | Geringer |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | Dejonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| D453,221 S | 1/2002 | Haytman et al. |
| 6,343,629 B1 | 2/2002 | Wessman et al. |
| 6,348,044 B1 | 2/2002 | Coletti et al. |
| 6,358,236 B1 | 3/2002 | Defoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,419,696 B1 | 7/2002 | Ortiz et al. |
| 6,440,107 B1 | 8/2002 | Trombley et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial et al. |
| 6,503,240 B1 | 1/2003 | Niedospial et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial |
| 6,551,299 B2 | 4/2003 | Miyoshi et al. |
| 6,558,365 B2 | 5/2003 | Zinger et al. |
| 6,569,196 B1 | 5/2003 | Vesely |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,581,648 B1 | 6/2003 | Zolentroff et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,699,232 B2 | 3/2004 | Hart et al. |
| 6,706,022 B1 | 3/2004 | Einsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Amnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Einsing et al. |
| 6,832,994 B2 | 12/2004 | Niedospial et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | Mcfarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,953,450 B2 | 10/2005 | Baldwin et al. |
| 6,957,745 B2 | 10/2005 | Thibault et al. |
| 6,960,164 B2 | 11/2005 | O'Heeron |
| 6,964,684 B2 | 11/2005 | Ortiz et al. |
| 6,972,002 B2 | 12/2005 | Thorne |
| 6,979,318 B1 | 12/2005 | Mcdonald et al. |
| RE38,996 E | 2/2006 | Crawford et al. |
| 6,994,315 B2 | 2/2006 | Ryan et al. |
| 6,997,916 B2 | 2/2006 | Simas et al. |
| 6,997,917 B2 | 2/2006 | Niedospial et al. |
| 7,024,968 B2 | 4/2006 | Raudabough et al. |

(56) References Cited

U.S. PATENT DOCUMENTS

| | | |
|---|---|---|
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,097,637 B2 | 8/2006 | Triplett et al. |
| 7,100,890 B2 | 9/2006 | Cote et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| D546,450 S | 7/2007 | Wolf |
| 7,241,285 B1 | 7/2007 | Dikeman |
| 7,294,122 B2 | 11/2007 | Kubo et al. |
| 7,306,199 B2 | 12/2007 | Leinsing et al. |
| D560,815 S | 1/2008 | Tajima |
| D561,348 S | 2/2008 | Zinger et al. |
| 7,326,188 B1 | 2/2008 | Russell et al. |
| 7,326,194 B2 | 2/2008 | Zinger et al. |
| 7,335,213 B1 | 2/2008 | Hyde et al. |
| 7,350,764 B2 | 4/2008 | Raybuck |
| 7,354,422 B2 | 4/2008 | Riesenberger et al. |
| 7,354,427 B2 | 4/2008 | Fangrow |
| D573,250 S | 7/2008 | Macrae et al. |
| D575,314 S | 8/2008 | Hind |
| 7,425,209 B2 | 9/2008 | Fowles et al. |
| 7,435,246 B2 | 10/2008 | Zihlmann |
| D580,558 S | 11/2008 | Shigesada et al. |
| D581,529 S | 11/2008 | Moehle et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,500,961 B2 | 3/2009 | Nemoto |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,569,062 B1 | 8/2009 | Kuehn et al. |
| D604,837 S | 11/2009 | Crawford et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| D609,804 S | 2/2010 | Uchida et al. |
| 7,654,995 B2 | 2/2010 | Warren et al. |
| 7,670,326 B2 | 3/2010 | Shemesh |
| 7,695,445 B2 | 4/2010 | Yuki |
| 7,703,483 B2 | 4/2010 | Hartman et al. |
| 7,704,229 B2 | 4/2010 | Moberg et al. |
| 7,704,236 B2 | 4/2010 | Denolly |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt et al. |
| D624,641 S | 9/2010 | Boclet |
| 7,799,009 B2 | 9/2010 | Niedospial et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,887,583 B2 | 2/2011 | Macoviak |
| 7,895,216 B2 | 2/2011 | Longshaw et al. |
| D634,007 S | 3/2011 | Zinger et al. |
| 7,896,849 B2 | 3/2011 | Delay |
| 7,900,659 B2 | 3/2011 | Whitley et al. |
| 7,914,499 B2 | 3/2011 | Gonnelli et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 7,993,328 B2 | 8/2011 | Whitley |
| 8,007,461 B2 | 8/2011 | Huo et al. |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| D671,654 S | 11/2012 | Akamatsu et al. |
| 8,317,741 B2 | 11/2012 | Kraushaar |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| 8,394,080 B2 * | 3/2013 | Jepson .......... A61M 39/26 604/537 |
| D681,230 S | 4/2013 | Mosler et al. |
| 8,418,690 B2 | 4/2013 | Power et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D689,605 S | 9/2013 | Bellenoit |
| D690,009 S | 9/2013 | Schembre et al. |
| D690,418 S | 9/2013 | Rosenquist |
| 8,523,837 B2 | 9/2013 | Wiggins et al. |

(56) References Cited

U.S. PATENT DOCUMENTS

| | | |
|---|---|---|
| D691,264 S | 10/2013 | Dallemagne et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili et al. |
| 8,667,996 B2 * | 3/2014 | Gonnelli ............... A61J 1/2089 604/407 |
| D703,812 S | 4/2014 | Cederschiold et al. |
| 8,684,992 B2 | 4/2014 | Sullivan et al. |
| 8,684,994 B2 | 4/2014 | Lev et al. |
| 8,752,598 B2 | 6/2014 | Denenburg et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |
| D720,451 S | 12/2014 | Denenburg et al. |
| D720,452 S | 12/2014 | Jordan |
| 8,900,212 B2 | 12/2014 | Kubo |
| 8,905,994 B1 | 12/2014 | Lev et al. |
| 8,915,882 B2 | 12/2014 | Cabiri |
| D720,850 S | 1/2015 | Hsia et al. |
| 8,986,370 B2 | 3/2015 | Annest |
| 9,011,522 B2 | 4/2015 | Annest |
| D732,660 S | 6/2015 | Ohashi |
| D732,664 S | 6/2015 | Wochr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,393,365 B2 | 7/2016 | Cabiri |
| D765,837 S | 9/2016 | Lev et al. |
| D767,124 S | 9/2016 | Lev et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| D833,599 S | 11/2018 | Nilsson et al. |
| D836,324 S | 12/2018 | Michalski |
| 10,206,854 B2 | 2/2019 | Wu et al. |
| D849,936 S | 5/2019 | Allard |
| D851,240 S | 6/2019 | Baid |
| 10,413,662 B2 | 9/2019 | Yeh et al. |
| D881,389 S | 4/2020 | Wang et al. |
| D881,390 S | 4/2020 | Wang et al. |
| 10,772,798 B2 | 9/2020 | Lev et al. |
| D903,836 S | 12/2020 | Pak et al. |
| D923,782 S | 6/2021 | Lev et al. |
| D923,812 S | 6/2021 | Ben |
| 2001/0047150 A1 | 11/2001 | Chobotov |
| 2002/0017328 A1 | 2/2002 | Loo |
| 2002/0029080 A1 | 3/2002 | Mortier et al. |
| 2002/0055711 A1 | 5/2002 | Lavi et al. |
| 2002/0065488 A1 | 5/2002 | Suzuki et al. |
| 2002/0087118 A1 | 7/2002 | Reynolds et al. |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0069550 A1 | 4/2003 | Sharp |
| 2003/0073971 A1 | 4/2003 | Saker |
| 2003/0083742 A1 | 5/2003 | Spence et al. |
| 2003/0100866 A1 | 5/2003 | Reynolds |
| 2003/0120209 A1 | 6/2003 | Jensen et al. |
| 2003/0135159 A1 | 7/2003 | Daily et al. |
| 2003/0187420 A1 | 10/2003 | Akerlund et al. |
| 2003/0195479 A1 | 10/2003 | Kuracina et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0044327 A1 | 3/2004 | Hasegawa |
| 2004/0044406 A1 | 3/2004 | Woolfson et al. |
| 2004/0073189 A1 | 4/2004 | Wyatt et al. |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162515 A1 | 8/2004 | Chornenky et al. |
| 2004/0162540 A1 | 8/2004 | Walenciak et al. |
| 2004/0167472 A1 | 8/2004 | Howell et al. |
| 2004/0181192 A1 | 9/2004 | Cuppy |
| 2004/0186424 A1 | 9/2004 | Hjertman |
| 2004/0204699 A1 | 10/2004 | Hanly et al. |
| 2004/0217315 A1 | 11/2004 | Doyle |
| 2004/0236419 A1 | 11/2004 | Milo |
| 2004/0255952 A1 | 12/2004 | Carlsen et al. |
| 2005/0010287 A1 | 1/2005 | Macoviak et al. |
| 2005/0015070 A1 | 1/2005 | Delnevo et al. |
| 2005/0055008 A1 | 3/2005 | Paradis et al. |
| 2005/0070999 A1 | 3/2005 | Spence |
| 2005/0075727 A1 | 4/2005 | Wheatley |
| 2005/0082828 A1 | 4/2005 | Wicks et al. |
| 2005/0137523 A1 | 6/2005 | Wyatt et al. |
| 2005/0137566 A1 | 6/2005 | Fowles et al. |
| 2005/0137702 A1 | 6/2005 | Haug et al. |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0049209 A1 | 3/2006 | Baker |
| 2006/0058741 A1 | 3/2006 | Gallagher |
| 2006/0074484 A1 | 4/2006 | Huber |
| 2006/0089594 A1 | 4/2006 | Andau |
| 2006/0095015 A1 | 5/2006 | Hobbs et al. |
| 2006/0135948 A1 | 6/2006 | Varma |
| 2006/0155257 A1 | 7/2006 | Reynolds |
| 2006/0161192 A1 | 7/2006 | Young |
| 2006/0169348 A1 | 8/2006 | Yigal |
| 2006/0178646 A1 | 8/2006 | Harris et al. |
| 2006/0195029 A1 | 8/2006 | Shults et al. |
| 2006/0212004 A1 | 9/2006 | Atil |
| 2006/0224105 A1 | 10/2006 | Thorne et al. |
| 2006/0253084 A1 | 11/2006 | Nordgren |
| 2006/0259135 A1 | 11/2006 | Navia et al. |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0095856 A1 | 5/2007 | Vogel et al. |
| 2007/0106218 A1 | 5/2007 | Yodfat et al. |
| 2007/0112324 A1 | 5/2007 | Hamedi-Sangsari |
| 2007/0156112 A1 | 7/2007 | Walsh |
| 2007/0167912 A1 | 7/2007 | Causey et al. |
| 2007/0191760 A1 | 8/2007 | Iguchi et al. |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244461 A1 | 10/2007 | Fangrow |
| 2007/0244462 A1 | 10/2007 | Fangrow |
| 2007/0249995 A1 | 10/2007 | Van |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |

(56) References Cited

U.S. PATENT DOCUMENTS

| | | |
|---|---|---|
| 2007/0287953 A1 | 12/2007 | Ziv et al. |
| 2007/0299404 A1 | 12/2007 | Katoh et al. |
| 2008/0009822 A1 | 1/2008 | Enerson |
| 2008/0015496 A1 | 1/2008 | Hamedi-Sangsari |
| 2008/0039935 A1 | 2/2008 | Buch et al. |
| 2008/0077235 A1 | 3/2008 | Kirson |
| 2008/0125860 A1 | 5/2008 | Webler et al. |
| 2008/0135051 A1 | 6/2008 | Lee |
| 2008/0167713 A1 | 7/2008 | Bolling |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim et al. |
| 2008/0215015 A1 | 9/2008 | Cindrich et al. |
| 2008/0249473 A1 | 10/2008 | Rutti et al. |
| 2008/0249479 A1 | 10/2008 | Zinger et al. |
| 2008/0262609 A1 | 10/2008 | Gross et al. |
| 2008/0269687 A1 | 10/2008 | Chong et al. |
| 2008/0275407 A1 | 11/2008 | Scheurer |
| 2008/0287905 A1 | 11/2008 | Hiejima et al. |
| 2008/0294100 A1 | 11/2008 | De et al. |
| 2008/0306439 A1 | 12/2008 | Nelson et al. |
| 2008/0312634 A1 | 12/2008 | Helmerson et al. |
| 2009/0043253 A1 | 2/2009 | Podaima |
| 2009/0054852 A1 | 2/2009 | Takano et al. |
| 2009/0054969 A1 | 2/2009 | Salahieh et al. |
| 2009/0062767 A1 | 3/2009 | Van et al. |
| 2009/0076360 A1 | 3/2009 | Brister et al. |
| 2009/0082750 A1 | 3/2009 | Denenburg et al. |
| 2009/0139724 A1 | 6/2009 | Gray et al. |
| 2009/0143758 A1 | 6/2009 | Okiyama |
| 2009/0177178 A1 | 7/2009 | Pedersen |
| 2009/0187140 A1 | 7/2009 | Racz |
| 2009/0216103 A1 | 8/2009 | Brister et al. |
| 2009/0257306 A1 | 10/2009 | Coffeen et al. |
| 2009/0267011 A1 | 10/2009 | Hatton et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0030181 A1 | 2/2010 | Helle et al. |
| 2010/0036319 A1 | 2/2010 | Drake et al. |
| 2010/0042147 A1 | 2/2010 | Janovsky et al. |
| 2010/0049315 A1 | 2/2010 | Kirson |
| 2010/0070027 A1 | 3/2010 | Bonhoeffer et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0137831 A1 | 6/2010 | Tsals |
| 2010/0152658 A1 | 6/2010 | Hanson et al. |
| 2010/0160889 A1 | 6/2010 | Smith et al. |
| 2010/0161047 A1 | 6/2010 | Cabiri |
| 2010/0162548 A1 | 7/2010 | Leidig |
| 2010/0168664 A1 | 7/2010 | Zinger et al. |
| 2010/0241088 A1 | 9/2010 | Ranalletta et al. |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosler et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0172636 A1 | 7/2011 | Aasmul |
| 2011/0218511 A1 | 9/2011 | Yokoyama |
| 2011/0224640 A1 | 9/2011 | Kuehn et al. |
| 2011/0230856 A1 | 9/2011 | Kyle et al. |
| 2011/0264069 A1 | 10/2011 | Bochenko |
| 2011/0275988 A1 | 11/2011 | Davis et al. |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0059332 A1 | 3/2012 | Woehr et al. |
| 2012/0059346 A1 | 3/2012 | Sheppard et al. |
| 2012/0067429 A1 | 3/2012 | Mosler et al. |
| 2012/0071819 A1 | 3/2012 | Brueggemann et al. |
| 2012/0078214 A1 | 3/2012 | Finke et al. |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Wase et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Denenburg et al. |
| 2013/0253448 A1 | 9/2013 | Baron et al. |
| 2013/0289530 A1 | 10/2013 | Wyatt et al. |
| 2013/0315026 A1 | 11/2013 | Cheio et al. |
| 2013/0317472 A1 | 11/2013 | Finke |
| 2014/0096862 A1 | 4/2014 | Ancas |
| 2014/0102552 A1* | 4/2014 | Shemesh .................. A61J 1/20 137/315.01 |
| 2014/0150911 A1 | 6/2014 | Hanner et al. |
| 2014/0194854 A1 | 7/2014 | Tsals |
| 2014/0221940 A1 | 8/2014 | Clauson et al. |
| 2014/0276215 A1 | 9/2014 | Nelson et al. |
| 2014/0277052 A1 | 9/2014 | Haselby et al. |
| 2015/0082746 A1 | 3/2015 | Ivosevic et al. |
| 2015/0088078 A1 | 3/2015 | Lev et al. |
| 2015/0112297 A1 | 4/2015 | Lev et al. |
| 2015/0209230 A1 | 7/2015 | Lev et al. |
| 2015/0250681 A1 | 9/2015 | Lev et al. |
| 2015/0290390 A1 | 10/2015 | Ring et al. |
| 2015/0297839 A1 | 10/2015 | Sanders et al. |
| 2015/0297880 A1 | 10/2015 | Ogawa et al. |
| 2015/0305770 A1 | 10/2015 | Fill et al. |
| 2016/0081308 A1 | 3/2016 | Cary et al. |
| 2016/0081878 A1 | 3/2016 | Marks et al. |
| 2016/0088995 A1 | 3/2016 | Ueda et al. |
| 2016/0166824 A1 | 6/2016 | Lev et al. |
| 2016/0199569 A1 | 7/2016 | Yevmenenko et al. |
| 2016/0228644 A1 | 8/2016 | Cabiri |
| 2016/0287475 A1 | 10/2016 | Yevmenenko et al. |
| 2016/0367439 A1 | 12/2016 | Davis et al. |
| 2018/0008513 A1 | 1/2018 | Iibuchi et al. |
| 2018/0161243 A1 | 6/2018 | Ariagno et al. |
| 2018/0221572 A1 | 8/2018 | Schlitt et al. |
| 2018/0303720 A1 | 10/2018 | Kennard et al. |
| 2019/0083357 A1 | 3/2019 | David et al. |
| 2019/0117514 A1 | 4/2019 | Denenburg et al. |
| 2019/0133885 A1 | 5/2019 | Wu et al. |
| 2019/0343725 A1 | 11/2019 | Denenburg |
| 2020/0276084 A1 | 9/2020 | Denenburg |
| 2020/0282133 A1 | 9/2020 | Mason et al. |
| 2020/0330326 A1 | 10/2020 | Merchant et al. |
| 2020/0376194 A1 | 12/2020 | Fabrikant et al. |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| CN | 106413799 A | 2/2017 |
| CN | 306375580 S | 3/2021 |
| DE | 1064693 B | 9/1959 |
| DE | 1913926 A1 | 9/1970 |
| DE | 4122476 A1 | 1/1993 |
| DE | 4314657 A1 | 11/1994 |

(56) References Cited

FOREIGN PATENT DOCUMENTS

| | | |
|---|---|---|
| DE | 4408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 001126270-0001 | 8/2010 |
| EM | 001680703-0001 | 8/2010 |
| EM | 001680703-0002 | 8/2010 |
| EM | 002446062-0001 | 8/2010 |
| EM | 002446062-0002 | 8/2010 |
| EM | 000627237-0001 | 10/2010 |
| EM | 006630893-0001 | 8/2019 |
| EM | 008039507-0004 | 1/2021 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0426403 A1 | 5/1991 |
| EP | 0282545 B1 | 2/1992 |
| EP | 0518397 A1 | 12/1992 |
| EP | 0521460 A1 | 1/1993 |
| EP | 0582038 A2 | 2/1994 |
| EP | 0598918 A1 | 6/1994 |
| EP | 0637443 A1 | 2/1995 |
| EP | 0737467 A1 | 10/1996 |
| EP | 0761562 A1 | 3/1997 |
| EP | 0765652 A1 | 4/1997 |
| EP | 0765853 A1 | 4/1997 |
| EP | 0806597 A1 | 11/1997 |
| EP | 0814866 A1 | 1/1998 |
| EP | 0829248 A2 | 3/1998 |
| EP | 0856331 A2 | 8/1998 |
| EP | 0882441 A2 | 12/1998 |
| EP | 0887085 A2 | 12/1998 |
| EP | 0887885 A2 | 12/1998 |
| EP | 0897708 A2 | 2/1999 |
| EP | 0898951 A2 | 3/1999 |
| EP | 0960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| EP | 2416739 B1 | 6/2016 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| IL | 186290 | 1/2008 |
| IN | 331018-001-0001 | 6/2021 |
| JP | 03-062426 B2 | 9/1991 |
| JP | 03-205560 A | 9/1991 |
| JP | 04-329954 A | 11/1992 |
| JP | 06-050656 U | 7/1994 |
| JP | 08-000710 A | 1/1996 |
| JP | 09-104460 A | 4/1997 |
| JP | 09-104461 A | 4/1997 |
| JP | 10-118158 A | 5/1998 |
| JP | 10-504736 A | 5/1998 |
| JP | 11-503627 A | 3/1999 |
| JP | 11-319031 A | 11/1999 |
| JP | 2000-508934 A | 7/2000 |
| JP | 2000-237278 A | 9/2000 |
| JP | 2000-262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2003-513709 A | 4/2003 |
| JP | 2004-501721 A | 1/2004 |
| JP | 2004-097253 A | 4/2004 |
| JP | 2004-522541 A | 7/2004 |
| JP | 2004-267776 A | 9/2004 |
| JP | 2005-270629 A | 10/2005 |
| JP | 2005-537048 A | 12/2005 |
| JP | 2006-061421 A | 3/2006 |
| JP | 2008-220961 A | 9/2008 |
| JP | 2009-513294 A | 4/2009 |
| JP | 4329954 B2 | 9/2009 |
| JP | 2010-063622 A | 3/2010 |
| JP | 2010-179128 A | 8/2010 |
| JP | 2012-205769 A | 10/2012 |
| JP | 2013-520272 A | 6/2013 |
| JP | 2014-000220 A | 1/2014 |
| JP | 2015-211763 A | 11/2015 |
| JP | 2019-015749 A | 1/2019 |
| NO | 2009/087572 A1 | 7/2009 |
| WO | 86/01487 A1 | 3/1986 |
| WO | 86/01712 A1 | 3/1986 |
| WO | 86/05683 A1 | 10/1986 |
| WO | 90/03536 A1 | 4/1990 |
| WO | 94/03373 A1 | 2/1994 |
| WO | 95/07066 A1 | 3/1995 |
| WO | 95/07720 A1 | 3/1995 |
| WO | 95/13785 A1 | 5/1995 |
| WO | 96/00053 A1 | 1/1996 |
| WO | 96/09083 A1 | 3/1996 |
| WO | 96/29113 A1 | 9/1996 |
| WO | 97/36636 A1 | 10/1997 |
| WO | 98/32411 A1 | 7/1998 |
| WO | 98/37854 A1 | 9/1998 |
| WO | 99/61093 A1 | 12/1999 |
| WO | 01/02490 A1 | 1/2001 |
| WO | 01/28490 A1 | 4/2001 |
| WO | 01/30425 A1 | 5/2001 |
| WO | 01/32524 A1 | 5/2001 |
| WO | 01/60311 A1 | 8/2001 |
| WO | 01/89607 A2 | 11/2001 |
| WO | 01/91693 A2 | 12/2001 |
| WO | 02/02165 A2 | 1/2002 |
| WO | 02/09797 A1 | 2/2002 |
| WO | 02/32372 A1 | 4/2002 |
| WO | 02/36191 A2 | 5/2002 |
| WO | 02/66100 A2 | 8/2002 |
| WO | 02/89900 A1 | 11/2002 |
| WO | 03/51423 A2 | 6/2003 |
| WO | 03/70147 A2 | 8/2003 |
| WO | 03/79956 A1 | 10/2003 |
| WO | 2004/004806 A1 | 1/2004 |
| WO | 2004/041148 A1 | 5/2004 |
| WO | 2004/096113 A2 | 11/2004 |
| WO | 2005/002492 A1 | 1/2005 |
| WO | 2005/018703 A2 | 3/2005 |
| WO | 2005/041846 A2 | 5/2005 |
| WO | 2005/105014 A2 | 11/2005 |
| WO | 2005/120431 A1 | 12/2005 |
| WO | 2006/099441 A2 | 9/2006 |
| WO | 2006/124634 A1 | 11/2006 |
| WO | 2007/015233 A2 | 2/2007 |
| WO | 2007/017868 A1 | 2/2007 |
| WO | 2007/052252 A1 | 5/2007 |
| WO | 2007/079305 A2 | 7/2007 |
| WO | 2007/101772 A1 | 9/2007 |
| WO | 2007/105221 A1 | 9/2007 |
| WO | 2007/130809 A2 | 11/2007 |
| WO | 2008/068756 A2 | 6/2008 |

(56) References Cited

FOREIGN PATENT DOCUMENTS

| | | |
|---|---|---|
| WO | 2008/076459 A1 | 6/2008 |
| WO | 2008/081424 A2 | 7/2008 |
| WO | 2008/126090 A1 | 10/2008 |
| WO | 2008/135989 A1 | 11/2008 |
| WO | 2009/026443 A2 | 2/2009 |
| WO | 2009/029010 A1 | 3/2009 |
| WO | 2009/038860 A2 | 3/2009 |
| WO | 2009/040804 A2 | 4/2009 |
| WO | 2009/093249 A1 | 7/2009 |
| WO | 2009/112489 A1 | 9/2009 |
| WO | 2009/140511 A1 | 11/2009 |
| WO | 2009/146088 A1 | 12/2009 |
| WO | 2010/061743 A1 | 6/2010 |
| WO | 2010/078227 A1 | 7/2010 |
| WO | 2010/117471 A2 | 10/2010 |
| WO | 2010/117580 A1 | 10/2010 |
| WO | 2011/004360 A1 | 1/2011 |
| WO | 2011/024725 A1 | 3/2011 |
| WO | 2011/025719 A1 | 3/2011 |
| WO | 2011/039747 A1 | 4/2011 |
| WO | 2011/058545 A1 | 5/2011 |
| WO | 2011/058548 A1 | 5/2011 |
| WO | 2011/077434 A1 | 6/2011 |
| WO | 2011/090955 A1 | 7/2011 |
| WO | 2011/104711 A1 | 9/2011 |
| WO | 2011/132657 A1 | 10/2011 |
| WO | 2011/150037 A1 | 12/2011 |
| WO | 2011/156373 A1 | 12/2011 |
| WO | 2012/004784 A1 | 1/2012 |
| WO | 2012/004790 A2 | 1/2012 |
| WO | 2012/063230 A1 | 5/2012 |
| WO | 2012/143921 A1 | 10/2012 |
| WO | 2012/150587 A1 | 11/2012 |
| WO | 2013/001525 A1 | 1/2013 |
| WO | 2013/127813 A1 | 9/2013 |
| WO | 2013/134246 A1 | 9/2013 |
| WO | 2013/148435 A1 | 10/2013 |
| WO | 2013/156944 A1 | 10/2013 |
| WO | 2013/156994 A1 | 10/2013 |
| WO | 2014/033706 A2 | 3/2014 |
| WO | 2014/033710 A1 | 3/2014 |
| WO | 2014/099395 A1 | 6/2014 |
| WO | 2014/170888 A1 | 10/2014 |
| WO | 2014/174278 A1 | 10/2014 |
| WO | 2015/009746 A2 | 1/2015 |
| WO | 2015/019343 A1 | 2/2015 |
| WO | 2016/023590 A1 | 2/2016 |
| WO | 2017/203512 A1 | 11/2017 |
| WO | 2018/104930 A1 | 6/2018 |
| WO | 2018/104932 A1 | 6/2018 |
| WO | 2018/178971 A1 | 10/2018 |
| WO | 2020/222220 A1 | 11/2020 |

OTHER PUBLICATIONS

U.S. Appl. No. 14/391,792 by Lev, filed Oct. 10, 2014.
U.S. Appl. No. 14/423,595 by Lev, filed Feb. 24, 2015.
U.S. Appl. No. 14/423,612 by Lev, filed Feb. 24, 2015.
U.S. Appl. No. 14/425,582 by Lev, filed Mar. 3, 2015.
U.S. Appl. No. 14/504,979 by Lev, filed Oct. 2, 2014.
U.S. Appl. No. 14/784,300 by Lev, filed Oct. 14, 2015.
U.S. Appl. No. 14/888,590 by Marks, filed Nov. 2, 2015.
U.S. Appl. No. 29/438,134 by Lev, filed Nov. 27, 2012.
U.S. Appl. No. 29/438,141 by Gilboa, filed Nov. 27, 2012.
U.S. Appl. No. 29/478,723 by Lev, filed Jan. 8, 2014.
U.S. Appl. No. 29/478,726 by Lev, filed Jan. 8, 2014.
U.S. Appl. No. 29/502,037 by Lev, filed Sep. 11, 2014.
U.S. Appl. No. 29/502,053 by Lev, filed Sep. 11, 2014.
U.S. Appl. No. 29/544,969 by Ben Shalom, filed Nov. 9, 2015.
Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1page.
Vial2Bag Advanced™ 20mm Admixture , West Pharmaceutical Services Inc, Youtube, [post date Nov. 5, 2020], [Site seen Jan. 25, 2022], Seen at URL: https://www.youtube.com/watch?v=J0Am3mt5vn8 (Year: 2020).
Vial2Bag DC, downloaded from webpage: https://www.youtube.com/watch?v=FEOkg1xNBrs, Original posting date: Aug. 21, 2014, 1 page.
Written Opinion dated Aug. 16, 2012 in Int'l Application No. PCT/IL2012/000164.
Written Opinion of ISR dated Jun. 19, 2006 in Int'l Application No. PCT/IL2005/000376.
Written Opinion of the Int'l Searching Authority Issued Oct. 27, 2008 in Int'l Application No. PCT/US2008/070024.
Written Opinion of the ISR dated Oct. 17, 2009 in Int'l Application No. PCT/IL08/00517.
Youtube, "ADVCARE—Vial Direct to bag Spoke", first available Oct. 31, 2018 (https://www.youtube.com/watch?v=dd8ctggkrfM&feature=emb_title)(2018).
Youtube, "vial2Bag DC", first available Feb. 1, 2018, (https://www.youtube.com/watch?v=abSKPo5e_Hg) (Year:2018).
Youtube, "Vial2Bag.RTM. Needleless IV Transfer System from Helapet Ltd", first available Aug. 21, 2014 (https://www.youtube.com/watch?v=yFejsv0eemE) (Year: 2014).
Int'l Search Report Issued Mar. 12, 2009 in Int'l Application No. PCT/IL2008/001278.
Int'l Search Report Issued Mar. 27, 2009 in Int'l Application No. PCT/US2008/070024.
Int'l Search Report issued Jul. 12, 2011 in Int'l Application No. PCT/IL2011/000186.
Int'l Search Report issued Jul. 12, 2011 in Int'l Application No. PCT/IL2011/000187.
Int'l Search Report Issued Jul. 27, 2007 in Int'l Application No. PCT/IL2007/000343.
Int'l Preliminary Report on Patentability dated Aug. 24, 2015 in Int'l Application No. PCT/IL2014/050405.
Int'l Search Report and Written Opinion dated Jul. 21, 2020 in Int'l Application No. PCT/IL2020/050362.
Int'l Search Report and Written Opinion dated Mar. 29, 2019 in Int'l Application No. PCT/IB2018/059577.
Int'l Search Report and Written Opinion issued on May 4, 2011 in Int'l Application No. PCT/IL2010/001077.
Int'l Search Report dated Apr. 24, 2020 in Int'l Application No. PCT/US2020/050020.
Int'l Search Report dated Aug. 25, 2008 in Int'l Application No. PCT/IL2008/000517.
Int'l Search Report dated Jan. 22, 2013 in Int'l Application No. PCT/IL2012/000354.
Int'l Search Report dated Nov. 20, 2006 in Int'l Application No. PCT/IL2006/000881.
International Search Report and Written Opinion dated Oct. 17, 2014 in International Application No. PCT/IL2014/050680.
International Search Report dated Jan. 23, 2007 in Int'l Application No. PCT/IL/2006/001228.
International Search Report dated Mar. 30, 2011 in Int'l Application No. PCT/IL2010/000939.
International Search Report Issued Aug. 28, 2008 in Int'l Application No. PCT/IL2008/000606.
Intl Search Report dated Dec. 6, 2006 in Int'l Application No. PCT/IL2006/000912.
IV disposables sets catalogue, Cardinal Health, Alaris(Registered) products, SmartSite(Registered) access devices and accessories product No. 10013365, SmartSite add-on bag access device with spike adapter and needle-free valve bag access port, pp. 1-5, Fall edition (2007).
Kipp, "Plastic Material Data Sheets," retrieved from the Internet: http://www.knovel.com/web/portal/browse/display?_EXT_KNOVEL_DISPLAY_bookid=1023&VerticalID=0, retrieved on Feb. 9, 2011.
Merchant "An engineered control device for needle free reconstitution and transfer of compounded sterile intravenous Drug solutions for immediate use to assist in complying with United States Pharmacopeia Chapter <797> standard", Adv Care, 2 pages, 2018.

(56) References Cited

OTHER PUBLICATIONS

MixJect, downloaded from webpage: http://www.westpharma.com/en/products/Pages/MixjecLaspx, Download Date: Aug. 8, 2012, 1 page.
MixJet Product Information Sheet, downloaded from webpage: http://www.westpharma.com/SiteCollectionDocuments/Recon/mixject%20product%20sheet.pdf; 1 page.
Non-Vented Vial Access Pin with ULTRASITE.RM. Valve, B. Braun Medical, Inc. website and product description, 3 pages, Feb. 2006.
Notice of Allowance dated Jan. 12, 2016 in U.S. Appl. No. 14/385,212 by Lev.
Notice of Allowance dated Mar. 17, 2016 in U.S. Appl. No. 29/502,037 by Lev.
Novel Transfer, Mixing and Drug Delivery System, MOP Medimop Medical Projects Ltd. Catalog, 4 pages, Rev. 4, 2004.
Office Action dated Apr. 17, 2014 in CN Application No. 201080051201.4.
Office Action dated Apr. 2, 2013 in U.S. Appl. No. 13/505,790.
Office Action dated Apr. 20, 2010 in U.S. Appl. No. 11/997,569.
Office Action dated Apr. 9, 2015 in U.S. Appl. No. 13/883,289 by Lev.
Office Action dated Aug. 20, 2013 in U.S. Appl. No. 13/576,461 by Lev.
Office Action dated Aug. 24, 2015 in U.S. Appl. No. 14/366,306 by Lev.
Office Action dated Aug. 3, 2011 in JP Application No. 2008-525719.
Office Action dated Aug. 7, 2015 in JP Application No. 2015-529206.
Office Action dated Dec. 13, 2010 in U.S. Appl. No. 12/293,122.
Office Action dated Dec. 20, 2010 in U.S. Appl. No. 12/063,176.
Office Action dated Dec. 23, 2010 in U.S. Appl. No. 29/334,696.
Office Action dated Dec. 9, 2015 in U.S. Appl. No. 29/478,723 by Lev.
Office Action dated Dec. 9, 2015 in U.S. Appl. No. 29/478,726 by Lev.
Office Action dated Feb. 13, 2014 in U.S. Appl. No. 13/884,981 by Denenburg.
Office Action dated Feb. 20, 2009 in U.S. Appl. No. 11/694,297.
Office Action dated Feb. 22, 2005 in U.S. Appl. No. 10/062,796.
Office Action dated Feb. 7, 2011 in U.S. Appl. No. 12/783,194.
Office Action dated Jan. 17, 2014 in CN Application No. 201180006534.X.
Office Action dated Jan. 2, 2014 in U.S. Appl. No. 13/505,881 by Lev.
Office Action dated Jan. 2, 2015 in U.S. Appl. No. 29/438,141 by Gilboa.
Office Action dated Jan. 20, 2010 in JP Application No. 2007-510229.
Office Action dated Jan. 23, 2013 in U.S. Appl. No. 12/112,490 by Zinger.
Office Action dated Jan. 5, 2015 in U.S. Appl. No. 29/413,220 by Lev.
Article with picture of West Pharmaceutical Services' Vial2Bag Needleless System, [on-line]; !Sips Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Author unknown, Progressive Medical inc. is proud to announce the launch of West's VIAL2BAG Agvanced, Progressive Medinc ., [Post Date Oct. 23, 2020], [Site seen Jan. 25, 2022], Seen at URL: https://www.progressivemedinc.com/west-launches-vial2bag-advanced-20mm-admixture-device/ (Year: 2020).
Decision to Grant dated Apr. 12, 2010 in EP Application No. 08738307.1.
Drug Administration Systems product information sheets; http://www.westpharma.com/eu/en/products/Pages/Vial2Bag.aspx; pp. 1-3 (admitted prior art).
English translation of an Office Action dated Apr. 28, 2014 in JP Application No. 2013-537257.
English translation of an Office Action dated Aug. 28, 2014 in JP Application No. 2013-168885.
English translation of an Office Action dated Dec. 25, 2013 in CN Application No. 201180006530.1.
English translation of an Office Action dated Dec. 4, 2013 in CN Application No. 201080051210.3.
English translation of an Office Action dated Feb. 4, 2014 in JP Application No. 2012-554468.
English translation of an Office Action dated Jan. 9, 2014 in JP Application No. 2010-526421.
English translation of an Office Action dated Jul. 26, 2013 in JP Application No. 2012-538464.
English translation of an Office Action dated Jun. 19, 2013 in JP Application No. 2012-531551.
English translation of an Office Action dated Jun. 30, 2014 in CN Application No. 201180052962.6.
English translation of an Office Action dated Sep. 10, 2013 in JP Application No. 2012-554468.
Extended European Search Report dated Jun. 3, 2014 in EP Application No. 08781828.2.
Facebook "West Pharmaceutical Services, Inc.", first available Oct. 21, 2014 (https://www.facebook.com/westpharma/photos/710246859056351)(2014).
Grifols Vial Adapter Product Literature, 2 pages, Jan. 2002.
http://www.knovel.com/web/portal/browse/display?.sub.-EXT.sub.-KNOVEL.su-b.-DISPLAY.sub.-bookid=1023&VerticalID=0 [retrieved on Feb. 9, 2011].
http://www.westpharma.com/en/products/Pages/Mixject.aspx (admitted prior art), [Retrieved on Aug. 8, 2012].
http://www.westpharma.com/eu/en/products/Pages/Vial2Bag.aspx; Drug Adminsitration Systems product information sheets pp. 1-3.
http://www.westpharma.com/eu/SiteCollectionDocuments/Recon/mixject%20produ- ct%20sheet.pfg: MIXJECT product information sheet pp. 1, Sep. 10, 2010.
Int'l Preliminary Report on Patenability Issued Oct. 20, 2009 in Int'l Application No. PCT/IL2008/000517.
Int'l Preliminary Report on Patentability issued Jan. 14, 2014 in Int'l Application No. PCT/IL2012/050516.
Int'l Preliminary Report on Patentability issued May 6, 2008 in Int'l Application No. PCT/IL2006/001228.
Int'l Preliminary Report on Patentability issued May 12, 2014 in Int'l Application No. PCT/IL2013/050316.
Int'l Preliminary Report on Patentability issued Aug. 20, 2014 in Int'l Application No. PCT/IL2012/050407.
Int'l Preliminary Report on Patentability issued Aug. 28, 2012 in Int'l Application No. PCT/IL2011/000186.
Int'l Preliminary Report on Patentability issued Sep. 24, 2013 in Int'l Application No. PCT/IL2012/000354.
Int'l Preliminary Report on Patentability Issued Dec. 4, 2007 in Int'l Application No. PCT/IL2006/000912.
Int'l Preliminary Report on Patentability Issued Jun. 19, 2006 in Int'l Application No. PCT/IL2005/000376.
Int'l Preliminary Report on Patentability Issued Jun. 19, 2008 in Int'l Application No. PCT/IL2007/000343.
Int'l Search Report & Written Opinion issued on Mar. 7, 2012 in Int'l Application No. PCT/IL2011/000829.
Int'l Search Report and Written Opinion issued Mar. 6, 2012 in Int'l Application No. PCT/IL2011/000834.
Int'l Search Report and Written Opinion issued May 8, 2014 in Int'l Application No. PCT/IL2013/050706.
Int'l Search Report and Written Opinion issued Jul. 16, 2014 in Int'l Application No. PCT/IL2014/050327.
Int'l Search Report and Written Opinion issued Sep. 2, 2014 in Int'l Application No. PCT/IL2014/050405.
Int'l Search Report and Written Opinion issued Mar. 23, 2020 in Int'l Application No. PCT/IL2020/050048.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.

(56) References Cited

OTHER PUBLICATIONS

Int'l Search Report issued Mar. 17, 2011 in Int'l Application No. PCT/IL2010/000915; Written Opinion.
Int'l Search Report issued Mar. 18, 2013 in Int'l Application No. PCT/IL2012/050516.
Int'l Search Report issued Jun. 5, 2013 in Int'l Application No. PCT/IL2012/050407.
Int'l Search Report issued Jun. 19, 2013 in Int'l Application No. PCT/IL2013/050167.
Int'l Search Report issued Jul. 1, 2013 in Int'l Application No. PCT/IL2013/050180.
Int'l Search Report issued Jul. 26, 2013 in Int'l Application No. PCT/IL2013/050316.
Int'l Search Report issued Jul. 31, 2013 in Int'l Application No. PCT/IL2013/050313.
Int'l Search Report issued Aug. 16, 2012 in Int'l Application No. PCT/IL2012/000164.
Int'l Search Report Issued Oct. 17, 2005 in Int'l Application No. PCT/IL2005/000376.
Int'l Search Report issued 1017/2011 in Int'l Application No. PCT/IL2011/000511.
Int'l Search Report issued Nov. 25, 2010 in Int'l Application No. PCT/IL2010/000530.
Office Action dated Jul. 11, 2011 in U.S. Appl. No. 12/293,122.
Office Action dated Jul. 13, 2012 in U.S. Appl. No. 12/112,490 by Zinger.
Office Action dated Jul. 31, 2014 in U.S. Appl. No. 29/438,141 by Gilboa.
Office Action dated Jun. 1, 2010 in U.S. Appl. No. 11/568,421.
Office Action dated Jun. 14, 2012 in U.S. Appl. No. 29/376,980.
Office Action dated Jun. 15, 2011 in JP Application No. 2008-538492.
Office Action dated Jun. 15, 2012 in U.S. Appl. No. 29/413,170.
Office Action dated Jun. 21, 2012 in U.S. Appl. No. 12/596, 167.
Office Action dated Jun. 8, 2010 in U.S. Appl. No. 12/112,490 by Zinger.
Office Action dated Mar. 1, 2012 in CN Application No. 200880108283.4.
Office Action dated Mar. 10, 2015 in EP Application No. 12 812 395.7.
Office Action dated Mar. 13, 2012 in CA Application No. 2,563,643.
Office Action dated Mar. 17, 2015 in U.S. Appl. No. 14/504,979 by Lev.
Office Action dated Mar. 25, 2016 in U.S. Appl. No. 29/478,726 by Lev.
Office Action dated Mar. 28, 2016 in JP Application No. 2016-507113.
Office Action dated Mar. 6, 2012 in U.S. Appl. No. 12/678,928.
Office Action dated May 12, 2011 in U.S. Appl. No. 12/063, 176.
Office Action dated May 27, 2010 in U.S. Appl. No. 11/559, 152.
Office Action dated May 28, 2015 in U.S. Appl. No. 14/391,792 by Lev.
Office Action dated May 31, 2013 in U.S. Appl. No. 13/505,790.
Office Action dated May 6, 2014 in U.S. Appl. No. 13/505,881 by Lev.
Office Action dated Nov. 11, 2013 in IL Application No. 218730.
Office Action dated Nov. 28, 2013 in IN Application No. 4348/DELNP/2008.
Office Action dated Nov. 29, 2010 in U.S. Appl. No. 11/568,421.
Office Action dated Oct. 5, 2005 in U.S. Appl. No. 10/062,796.
Office Action dated Oct. 5, 2015 in U.S. Appl. No. 14/385,212 by Lev.
Office Action dated Oct. 6, 2003 in U.S. Appl. No. 10/062,796.
Office Action dated Oct. 8, 2013 in CN Application No. 201080043825.1.
Office Action dated Sep. 28, 2010 in U.S. Appl. No. 12/112,490 by Zinger.
Office Action issued Jul. 31, 2012 in U.S. Appl. No. 12/598,469.
Office Action issued May 25, 2021 issued in Japanese Application No. 2020-553506.
Our Vial2Bag Advanced™ 20mm admixture device , West Pharma, WestPharma @twitter, [Postdate 3/19/021], [Siteseen Jan. 25, 2022], Seen at URL: https://twitter.com/westpharma/status/1372921057766739971 (Year: 2021).
Overview—Silicone Rubber [retrieved from http://www.knovel.com/web/portal/browse/display?_EXT_KNOVEL_DISPLAY_bookid=1023&Vertica11D=0 on Feb. 9, 2011].
Photographs of Alaris Medical Systems SmartSite.RTM. device, 5 pages, 2002.
Publication dale of Israeli Patent Application 186290 [on-line]. ]Retrieved from Internet May 24, 2010]. URL:<http://www.ilpatsearch.justrice.gov.il/UI/Requestslistaspx>. (1 page).
Smart Site Needle-Free Systems, Alaris Medical Systems Webpage, 4 pages, Feb. 2006.
Smart Site.RTM. Alaris Medical Systems Product Brochure, 4 pages, Issue 1, Oct. 1999.
Summit International Medical Technologies Inc., Vial Direct to Bag Spike 2020.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Translation of Office Action dated Apr. 15, 2013 in JP Application No. 2008-538492.
Translation of Office Action dated Jun. 18, 2012 in JP Application No. 2008-538492.
U.S. Appl. No. 14/005,751 by Denenburg, filed Sep. 17, 2013.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
U.S. Appl. No. 13/883,289 by Lev, filed May 3, 2013.
U.S. Appl. No. 13/884,981 by Denenburg, filed May 13, 2013.
U.S. Appl. No. 14/345,094 by Lev, filed Mar. 14, 2014.
U.S. Appl. No. 14/366,306 by Lev, filed Jun. 18, 2014.

\* cited by examiner

LIQUID TRANSFER DEVICE WITH INTEGRATED SYRINGE

CROSS-REFERENCE TO RELATED APPLICATIONS

This application is a National Stage of International patent application no. PCT/IL2020/050362, filed on Mar. 26, 2020, which claims priority from U.S. Provisional Patent Application No. 62/831,214, titled "Liquid Transfer Device With Integrated Syringe", filed on Apr. 9, 2019, the entire contents of which are incorporated by reference herein.

BACKGROUND OF THE DISCLOSURE

The present disclosure is generally directed to liquid transfer devices.

Conventional infusion liquid containers containing an infusion liquid to be delivered to a patient generally take the form of an infusion liquid bag, an infusion liquid bottle, and the like. A pre-filled syringe or vial is generally utilized to add a high concentration of a drug to the infusion liquid contents, via a liquid transfer device, to form a diluted, medicated infusion liquid. Thereafter, an infusion set including an IV spike is generally inserted into an IV port of the liquid transfer device for infusion of medicated infusion liquid contents to a patient.

It would be advantageous to manufacture a liquid transfer device capable of flushing the flow path between the IV port and the port connected to the medicated infusion liquid contents between the step of adding/mixing the liquid drug to the infusion liquid contents and the step of administering the medicated infusion liquid contents to a patient, as an added measure to prevent the patient from receiving a portion of the drug in an undiluted, high concentration form.

BRIEF SUMMARY OF THE DISCLOSURE

Briefly stated, one aspect of the present disclosure is directed to a liquid transfer device configured for use with each of an infusion liquid container having an intravenous (IV) port, a vial sealed by a vial stopper, and an infusion set including an IV spike for sealing insertion into an IV port. The liquid transfer device includes a trifurcated connector body defining a barrel at a first end thereof, an IV spike at a second end thereof and a vial adapter lumen at a third end thereof. The barrel defines an internal chamber having an open proximal end. The IV spike defines an internal IV spike lumen having a distally located first aperture, and the IV spike is configured to sealingly insert into the IV port of the infusion liquid container. The vial adapter lumen branches off of the IV spike lumen. A vial adapter is secured to the vial adapter lumen and configured to mount onto the vial. The vial adapter includes a cannula fluidly connected with the vial adapter lumen and configured to puncture the vial stopper upon mounting of the vial adapter onto the vial for flow communication therewith. A plunger is in slidable engagement with the internal chamber of barrel via the open proximal end thereof. The plunger includes a piston face transversely oriented relative to, and in sealing engagement with, the barrel and a tube projecting proximally from the piston face and terminating in an IV port configured to sealingly receive the IV spike of the infusion set. The tube defines an internal plunger lumen therein. A plunger rod projects distally from the piston face and into the IV spike lumen. The plunger rod and the IV spike lumen define a fluid-flow pathway therebetween, the fluid-flow pathway being sealed off from the vial adapter lumen. A second aperture is interposed between a distal end of the internal chamber of the barrel and a proximal end of the IV spike lumen, and aligned with the fluid-flow pathway, to fluidly connect the fluid-flow pathway with the internal chamber of the barrel. In an advanced position of the plunger, the plunger rod seals off the vial adapter lumen from fluid communication with the IV spike lumen and the internal chamber of the barrel is in fluid communication with the IV spike lumen and the first aperture of the IV spike via the fluid-flow pathway and the second aperture. In a retracted position of the plunger, the plunger rod seals off the internal chamber of the barrel from fluid communication with the IV spike lumen and the first aperture of the IV spike, and the vial adapter lumen is fluidly communicated with the IV spike lumen and the first aperture of the IV spike.

Briefly stated, another aspect of the present disclosure is directed to a method of mixing a medicament additive contained within a vial and sealed by a vial stopper with an infusion liquid contained within an infusion liquid container, with a liquid transfer device, to form a medicated infusion liquid. The liquid transfer device includes a trifurcated connector body defining a barrel at a first end thereof, an IV spike at a second end thereof and a vial adapter lumen at a third end thereof, the barrel defines an internal chamber having an open proximal end. The IV spike defines an internal IV spike lumen having a distally located first aperture, and the vial adapter lumen branches off of the IV spike lumen. A vial adapter is secured to the vial adapter lumen, and includes a cannula fluidly connected with the vial adapter lumen. A plunger is in slidable engagement with the internal chamber of the barrel via the open proximal end thereof. The plunger includes a piston face transversely oriented relative to, and in sealing engagement with the barrel, and a tube projecting proximally from the piston face and terminating in an IV port. The tube defines an internal plunger lumen therein. A plunger rod projects distally from the piston face and into the IV spike lumen. The plunger rod and the IV spike lumen define a fluid-flow pathway therebetween, the fluid-flow pathway being sealed off from the vial adapter lumen. A second aperture is interposed between a distal end of the internal chamber of the barrel and a proximal end of the IV spike lumen, and aligned with the fluid-flow pathway to fluidly connect the fluid-flow pathway with the internal chamber of the barrel. In an advanced position of the plunger, the plunger rod seals off the vial adapter lumen from fluid communication with the IV spike lumen and the internal chamber of the barrel is in fluid communication with the IV spike lumen and the first aperture of the IV spike via the fluid-flow pathway and the second aperture. In a retracted position of the plunger, the plunger rod seals off the internal chamber of the barrel from fluid communication with the IV spike lumen and the first aperture of the IV spike, and the vial adapter lumen is fluidly communicated with the IV spike lumen and the first aperture of the IV spike. The method includes the steps of:
  (i) sealingly inserting the IV spike of the liquid transfer device into an IV port of the infusion liquid container;
  (ii) mounting the vial adapter onto the vial and puncturing the vial stopper for flow communication between the vial and the vial adapter lumen;
  (iii) withdrawing the plunger proximally through the internal chamber of the barrel, from the advanced position thereof toward the retracted position thereof, and, in turn, pulling a volume of the infusion liquid into the internal chamber of the barrel;

(iv) sealing off the internal chamber of the barrel from fluid communication with the IV spike lumen and the first aperture of the IV spike upon reaching the retracted position of the plunger;

(v) combining the medicament additive contained within the vial with the infusion liquid within the infusion liquid container via fluid communication between the vial adapter lumen, the IV spike lumen and the first aperture of the IV spike when the plunger is in the retracted position, to form a medicated infusion liquid; and (vi) depressing the plunger distally through the internal chamber to re-seal the vial adapter lumen from fluid communication with the IV spike lumen, re-communicate the internal chamber of the barrel with the IV spike lumen and the first aperture of the IV spike, and push out the volume of the infusion liquid within the internal chamber through the IV spike lumen, out of the first aperture and into the infusion liquid container.

BRIEF DESCRIPTION OF THE DRAWINGS

The following description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1A:
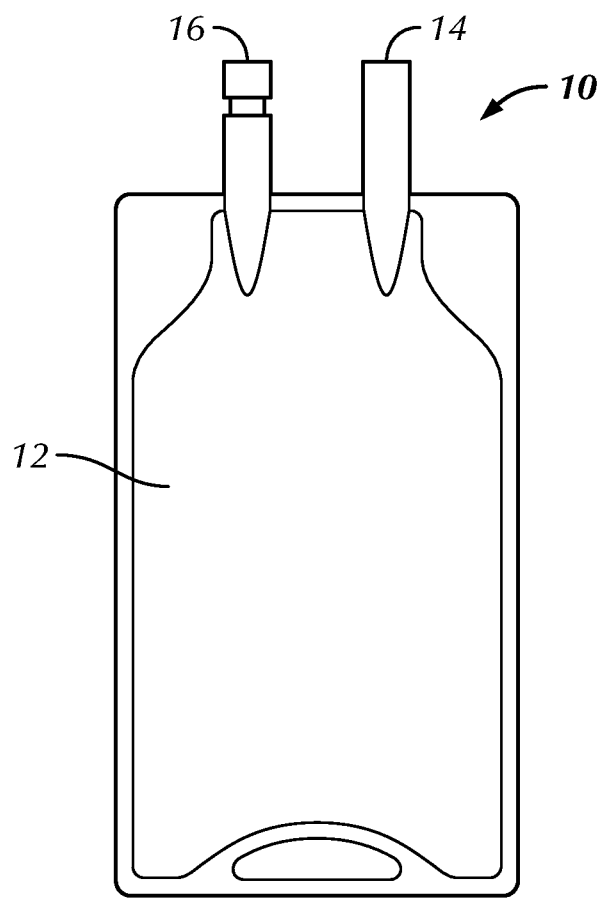
FIG. 1A is a front elevational view of an infusion bag usable with a liquid transfer device according to the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the liquid transfer device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1B:
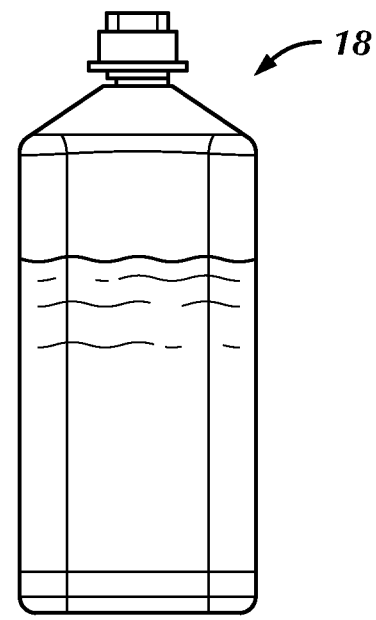
FIG. 1B is a front elevational view of an IV bottle usable with a liquid transfer device according to the present disclosure.
Figure 1C:
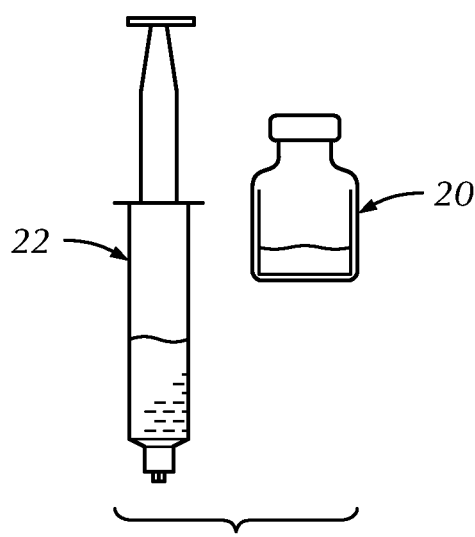
FIG. 1C is a front elevational view of a pre-filled needleless syringe and a vial usable with the liquid transfer device according to the present disclosure.

Referring to the drawings in detail, wherein like numerals indicate like elements throughout, there is shown in FIGS. 2-5D, a configuration of a liquid transfer device 30 intended for use with the combination of infusion liquid containers containing an infusion liquid and additive transfer devices. In the illustrated embodiment, the liquid transfer device 30 is intended for use with an infusion liquid container in the form of an infusion liquid bag 10 (FIG. 1A). As should be understood by those of ordinary skill in the art, a conventional infusion liquid bag 10 includes a reservoir 12 containing infusion liquid, in fluid communication with an intravenous (IV) or administration port 14 and an additive port 16. The infusion liquid bag 10 is collapsible upon administration of the infusion liquid therefrom. The liquid transfer device 30 may also, however, take a different configuration intended for use with an infusion liquid container in the form of an infusion liquid bottle 18 (FIG. 1B) or the like. The liquid transfer device 30 of the illustrated embodiment is also intended for use with an additive transfer device in the form of a sealed vial 20 (FIG. 1C). The vial 20 generally contains a medicament liquid additive or a lyophilized powder drug requiring reconstitution prior to administration to a patient, i.e., requiring mixing with the infusion liquid in the bag 10 to form a medicated infusion liquid administered to a patient. The contents of the vial 20 are, therefore, introduced into the infusion liquid bag 10 via the liquid transfer device 30 (as will be described in further detail below). The liquid transfer device 30 may also, however, take a different configuration intended for use with a syringe 22 (FIG. 1C).

The liquid transfer device 30 includes a trifurcated connector body 32. In the illustrated configuration, the trifurcated connector body 32 includes a barrel 34 at a first end thereof, an IV spike 36 at a second end thereof, and a vial adapter 38 at a third end thereof, but the disclosure is not so limited (as described further below). The barrel 34 defines an internal chamber 34a having an open proximal end 34b for slidably receiving a plunger 40 (as will be described further below). The IV spike 36 at the second end of the trifurcated body 32 enables use of the liquid transfer device 30 with infusion liquid bags 10, i.e., for sealingly inserting the IV spike 36 into the IV port 14 of the bag 10. The IV spike 36 may be constructed from a suitable rigid metal, polymeric or plastic material, such as, for example, polycarbonate and the like. As shown best in FIGS. 3B, 3C, 4B, 4C, 5B and 5C, the IV spike 36 is co-directional with the barrel 34 and includes an internal liquid lumen 36a in fluid communication with the chamber 34a. Distal apertures 36b are peripherally disposed proximate the spike end 36c thereof. A flange 33 extends laterally from the IV spike 36 proximate an opposing end thereof, for restricting insertion depth into the IV port 14 of the bag 10. In one embodiment, the barrel 34 is integrally formed as an injection molded monolithic structure with the flange 33, but the disclosure is not so limited. A spike cap 35 (FIG. 3D) may removably cover the IV spike 36 when not in use.

A vial adapter lumen 37 angularly bifurcates from, i.e., branches off of, the IV spike lumen 36a and leads to the vial adapter 38. The vial adapter 38 is configured to mount onto a vial 20 to enable usage of the device 30 with an additive transfer device in the form of a vial 20. In the illustrated configuration, the vial adapter 38 is integrally formed at the third end of the connector body 32, but the disclosure is not so limited. The vial adapter 38 includes a flexible skirt 38a for telescopic snap fit mounting onto a vial 20 (in a standard manner) and a cannula 38b for puncturing the vial 20, e.g., via a stopper thereof, to fluidly communicate therewith. The puncturing cannula 38b includes a lumen 38c in fluid communication with the vial adapter lumen 37, and, in turn with the IV spike lumen 36a.

Figure 2:
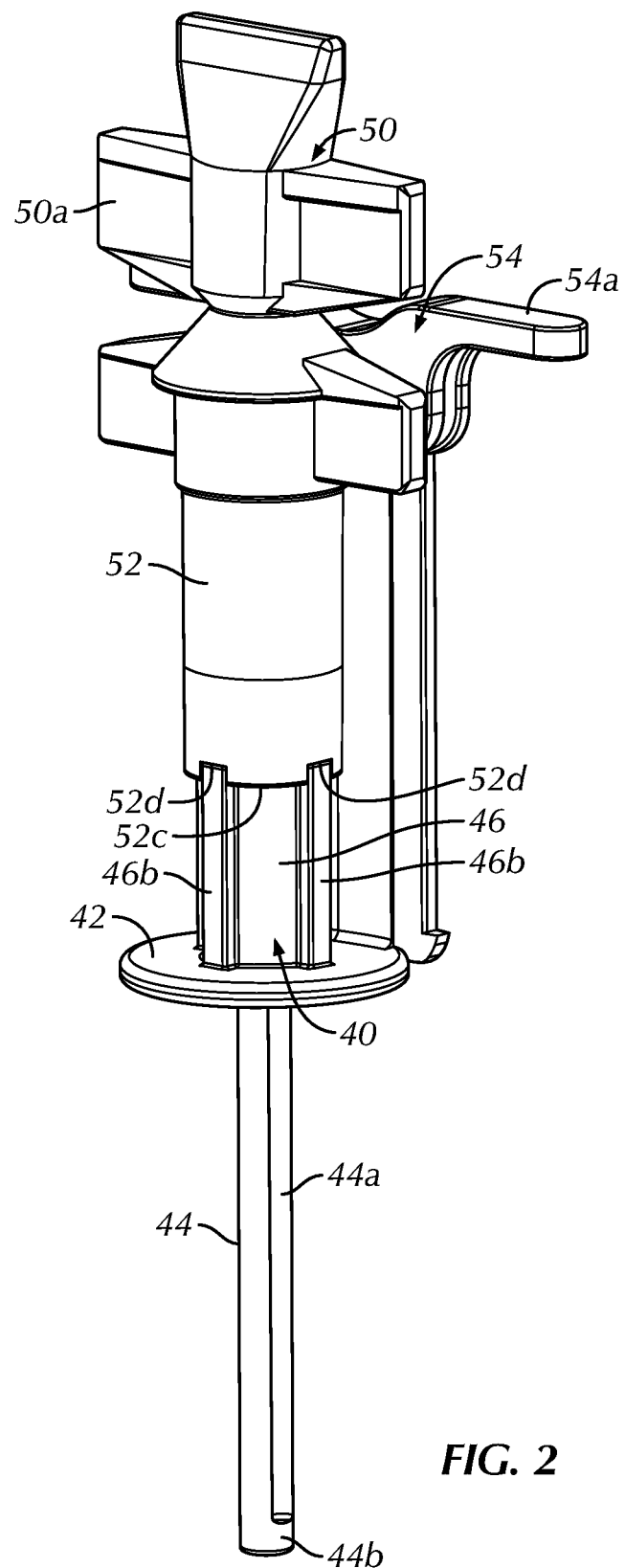
FIG. 2 is a perspective view of a syringe plunger and an IV port of the liquid transfer device according to the present disclosure.

As shown best in FIG. 2, the plunger 40 includes a transverse piston face 42 positioned within the barrel chamber 34a (FIGS. 3B, 3C, 4B, 4C, 5B and 5C) and complementary in shape to the inner sidewall of the barrel chamber 34a, permitting sliding therein while creating a substantially air-tight seal with the sidewall. A plunger rod 44 extends distally from the piston face 42 and into the IV spike lumen 36a. An upright plunger tube 46 projects proximally from the piston face 42, having a plunger lumen 46a therein and terminating in a barbed fitting member 48 having an open end 48a.

An IV port 50 is fluidly connected with the plunger tube 46 via the barbed fitting member 48. As shown best in FIGS. 2, 3A, 3D, 4A, 4D, 5A and 5D, the IV port 50 includes a twist-off member 50a proximate a peripheral, free proximal end of the port 50, and an elongate connecting member 52 projecting distally therefrom, having an internal lumen 52a extending therethrough and terminating in an open end 52c (opposite end from the twist-off member 50a). The internal lumen 52a of the IV port 50 extends co-directionally with the plunger lumen 46a. In one embodiment, the IV port 50 may be constructed from a suitable flexible polymeric or plastic material, such as, for example, PVC, and the like. The IV port 50 includes a septum 50b positioned within the elongate connecting member 52 (see FIGS. 3B, 4B, 5B), sealing across the internal lumen 52a. Accordingly, the twist-off member 50a may be removed without leading to flow communication beyond the septum 50b. Flow communication beyond the septum 50b, i.e., with the plunger lumen 46a and beyond, is only achieved upon puncturing fully through the septum 50b (as described in further detail below). The twist off member 50a keeps the septum 50b sterile until use.

The barbed fitting member 48 is configured, i.e., size, dimension, material, relative to the internal diameter and material of the elongate connecting member 52 to advance into the internal lumen 52a through the open end 52c, and form a barbed, friction, i.e., interference, fit therebetween. As should be understood by those of ordinary skill in the art, the barbed fitting member 48 permits advancement thereof into the internal lumen 52a to sealingly and securely mount the IV port 50 co-directionally upon the plunger tube 46, and also substantially prevent withdrawal of the barbed fitting member 48 without damaging at least one of the elongate connecting member 52 and the barbed fitting member 48. That is, and as shown, the barbed fitting member 48 is frustoconically shaped, having a progressively increasing diameter in a direction away from the open end 48a. An opposing end of the barbed fitting member 48 defines a greater diameter from the underlying plunger tube 46, resulting in an annular rib 48b that bites into the interior sidewall of the elongate connecting member 52, upon attempted withdrawal of the barbed fitting member 48 out of the elongate connecting member 52. Accordingly, the barbed fitting member 48 is advanceable into the internal lumen 52a of the elongate connecting member 52 during assembly, and, thereafter, is not readily able to be withdrawn without causing damage.

As shown best in FIG. 2, the rim of the elongate connecting member 52 defining the open end 52c thereof includes at least one cutout 52d, and the plunger tube 46 includes a corresponding at least one rib 46b along an external periphery thereof and configured to mate with an opposing cutout 52d. In the illustrated embodiment, the rib 46b is elongate but may alternatively take the form of a tab or the like. In the illustrated embodiment, the elongate connecting member 52 includes a plurality of angularly spaced cutouts 52d, and the plunger tube 46 includes a corresponding plurality of angularly spaced ribs 46b. The rib(s) 46b mates with the cutout(s) 52d during mounting of the IV port 50 upon the barbed fitting member 48 to sealingly and rotationally fix the IV port 50 relative to the plunger tube 46, and, thereby to the remainder of the liquid transfer device 30. As should be understood by those of ordinary skill in the art, however, the IV port 50 may additionally or alternatively be adhesively bonded (or the like) to the plunger tube 46.

Figure 3A:
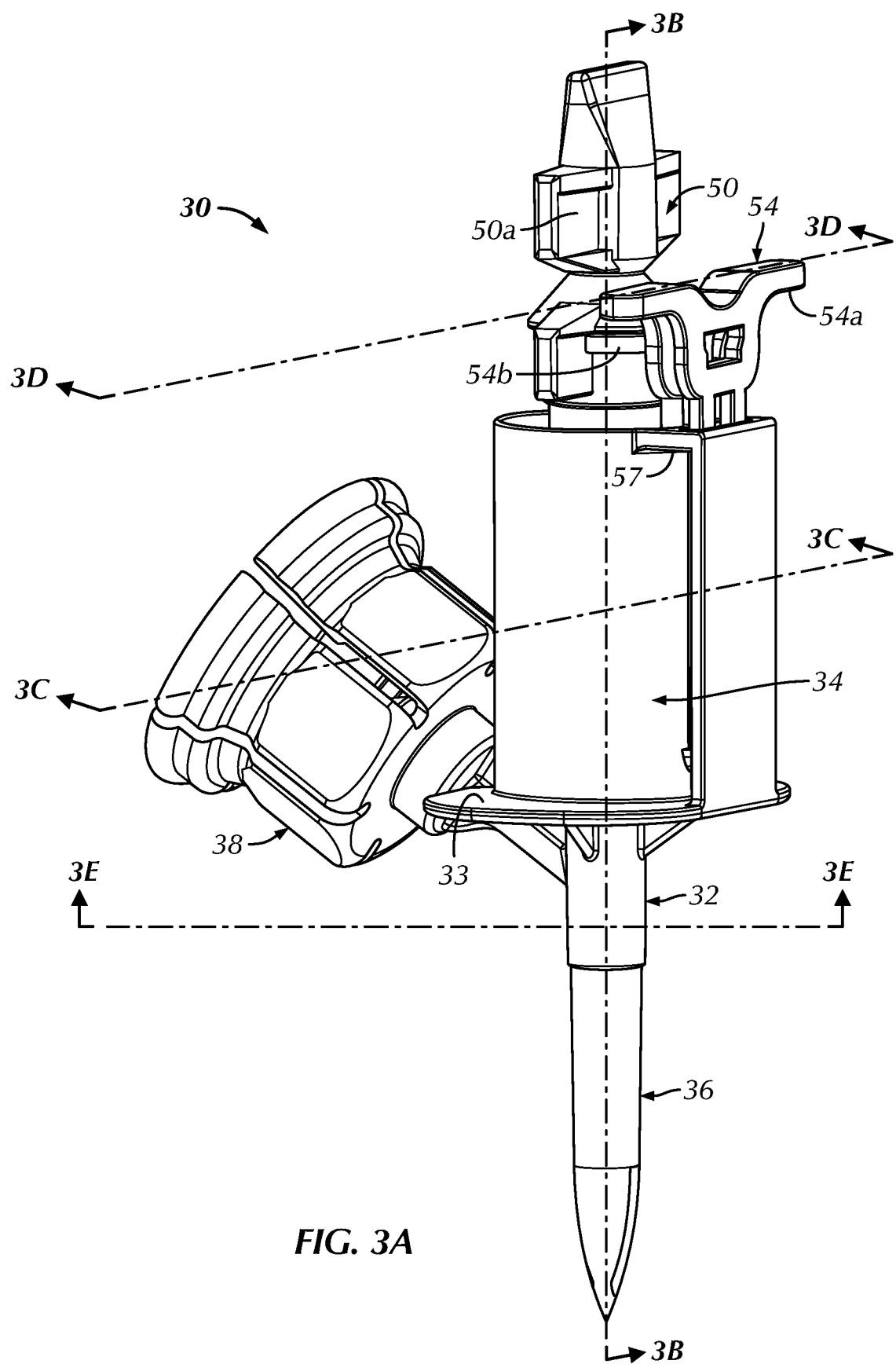
FIG. 3A is a perspective view of a configuration of the liquid transfer device according to the present disclosure, in a partially-locked, pre-mixing configuration.
Figure 3B:
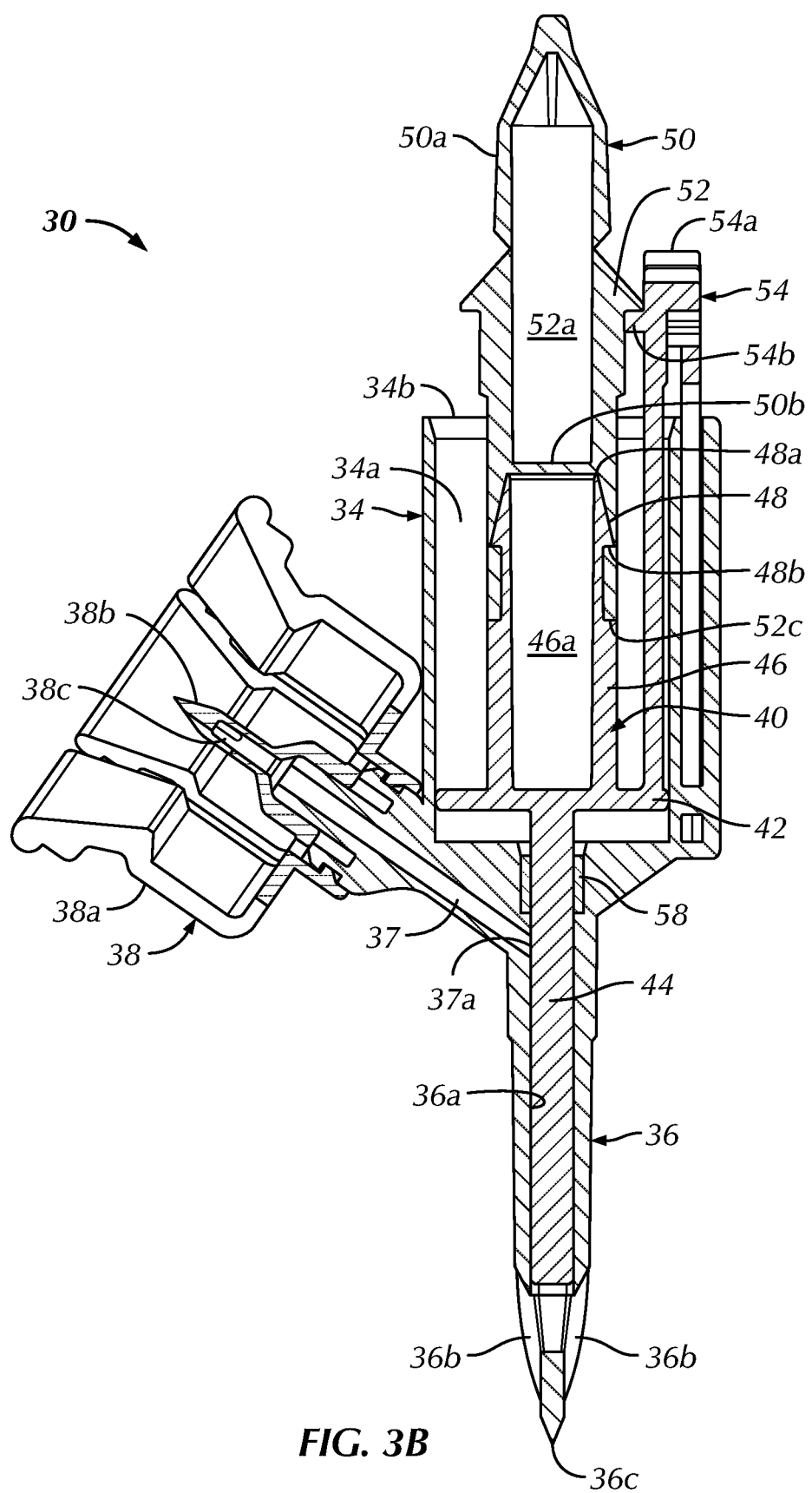
FIG. 3B is a cross-sectional elevational view of the liquid transfer device of FIG. 3A, taken along sectional line 3B-3B of FIG. 3A.
Figure 3C:
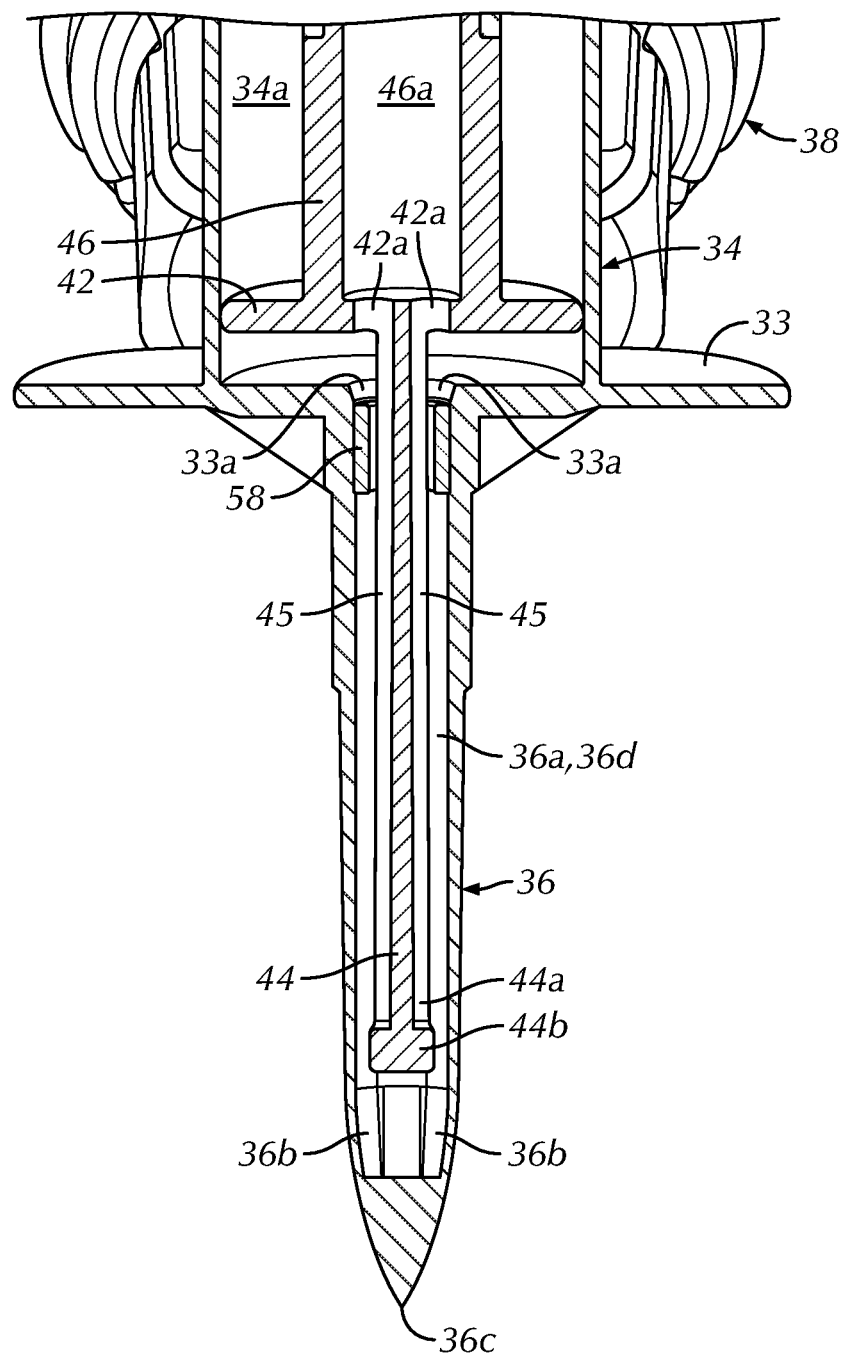
FIG. 3C is a partial, cross-sectional elevational view of the liquid transfer device of FIG. 3A, taken along sectional line 3C-3C of FIG. 3A.
Figure 4A:
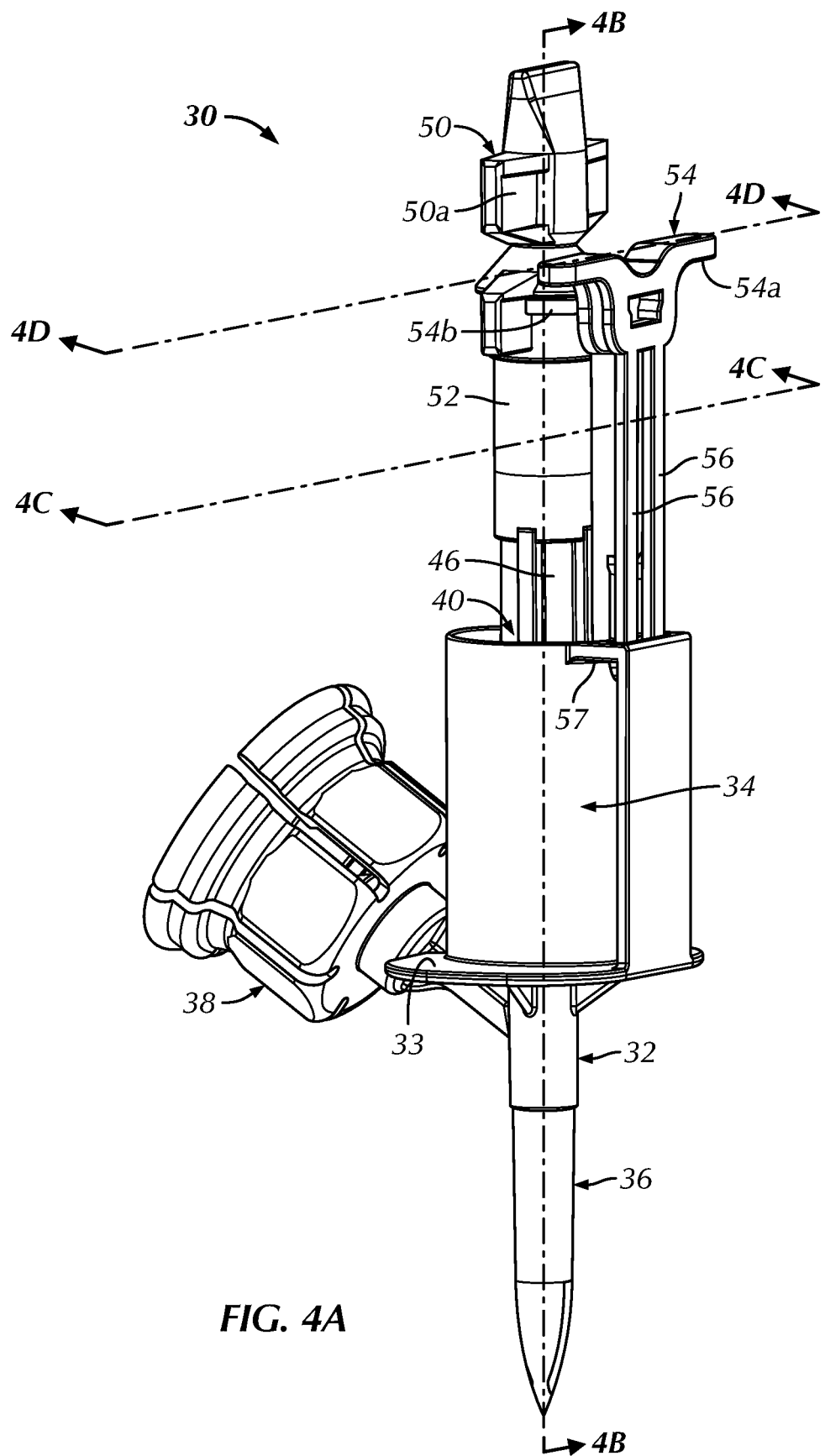
FIG. 4A is a perspective view of the liquid transfer device according to the present disclosure, in a ready-to-mix configuration.
Figure 4B:
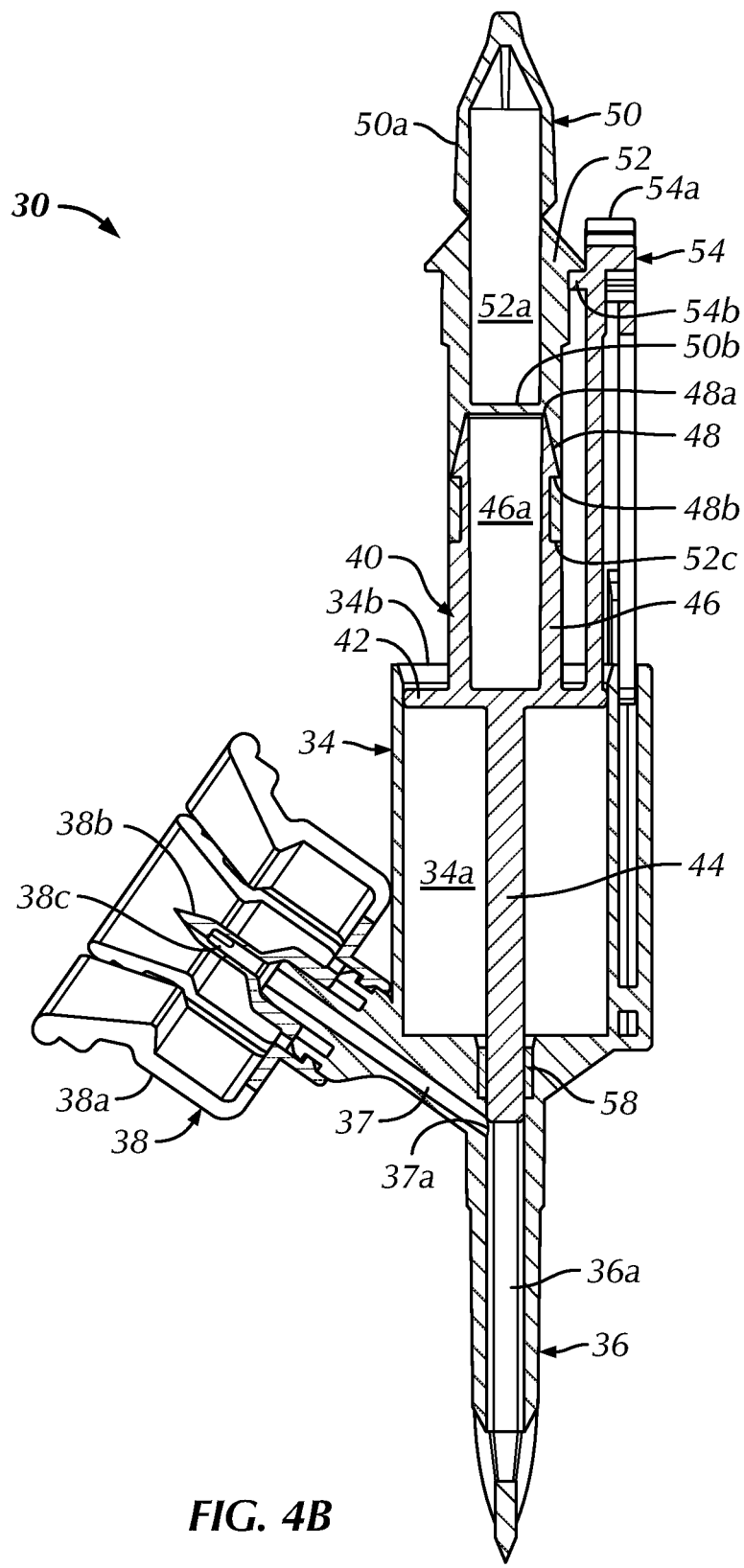
FIG. 4B is a cross-sectional elevational view of the liquid transfer device of FIG. 4A, taken along sectional line 4B-4B of FIG. 4A.
Figure 4C:
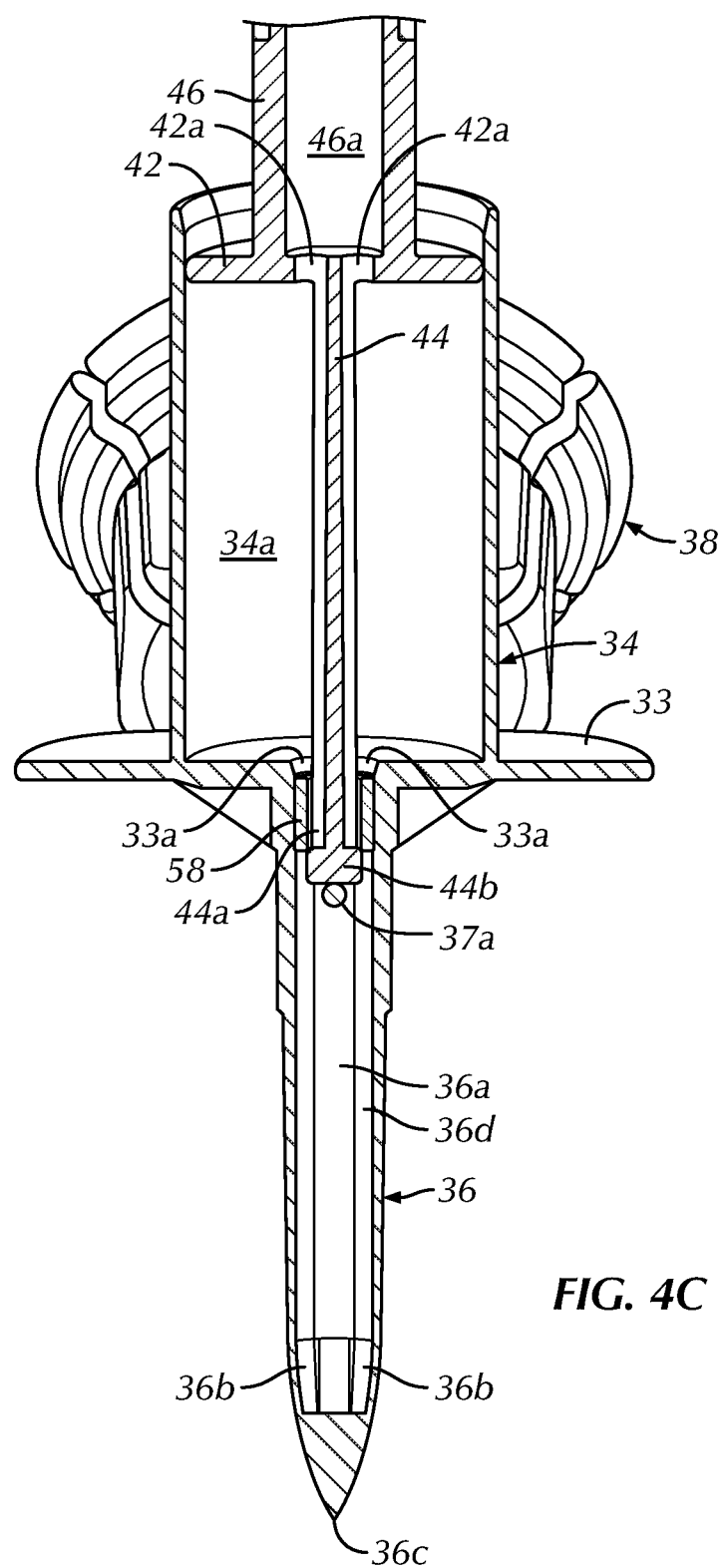
FIG. 4C is a partial, cross-sectional elevational view of the liquid transfer device of FIG. 4A, taken along sectional line 4C-4C of FIG. 4A.
Figure 5A:
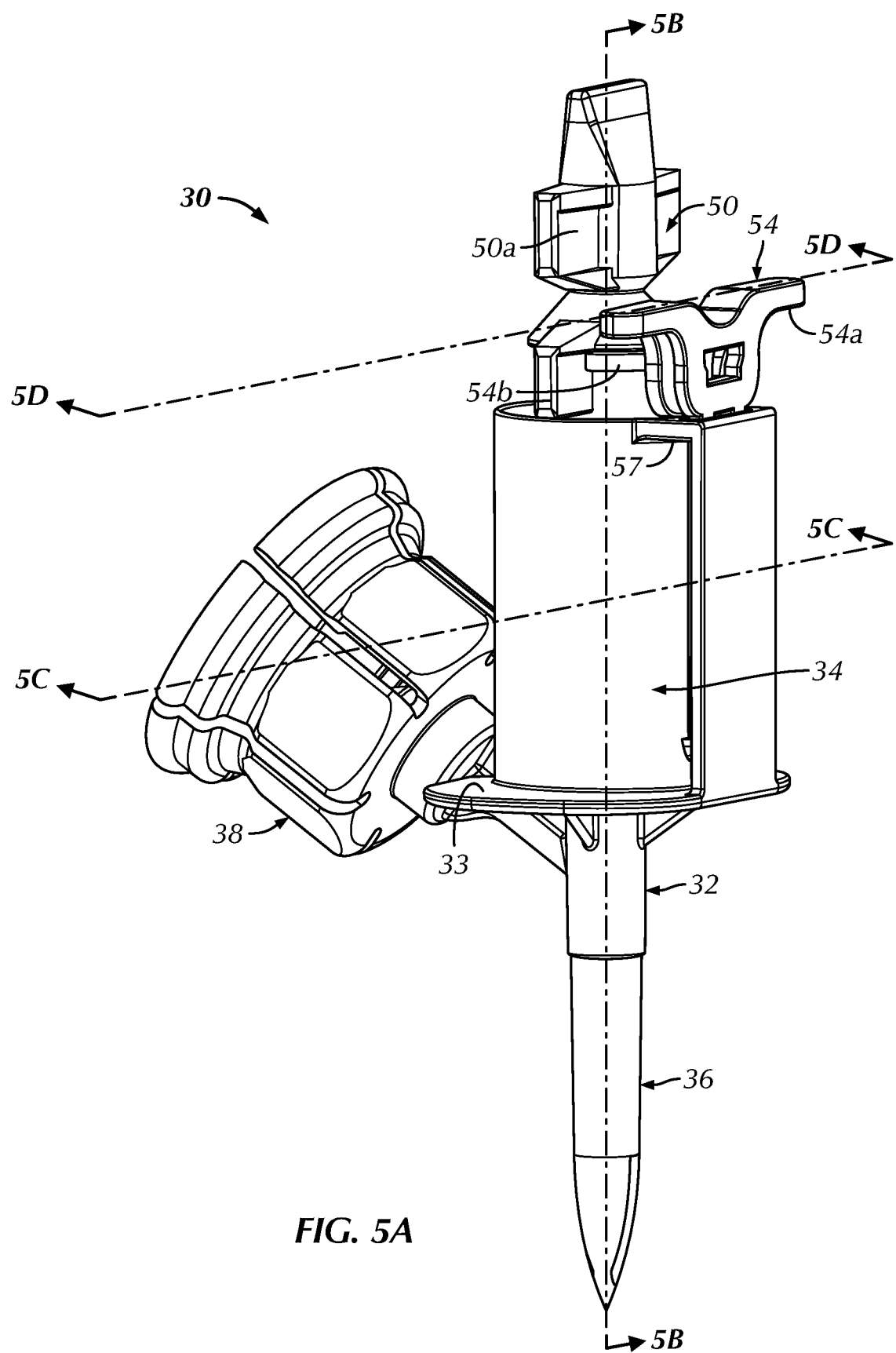
FIG. 5A is a perspective view of the liquid transfer device according to the present disclosure, in a fully-locked, post-mixing configuration.
Figure 5B:
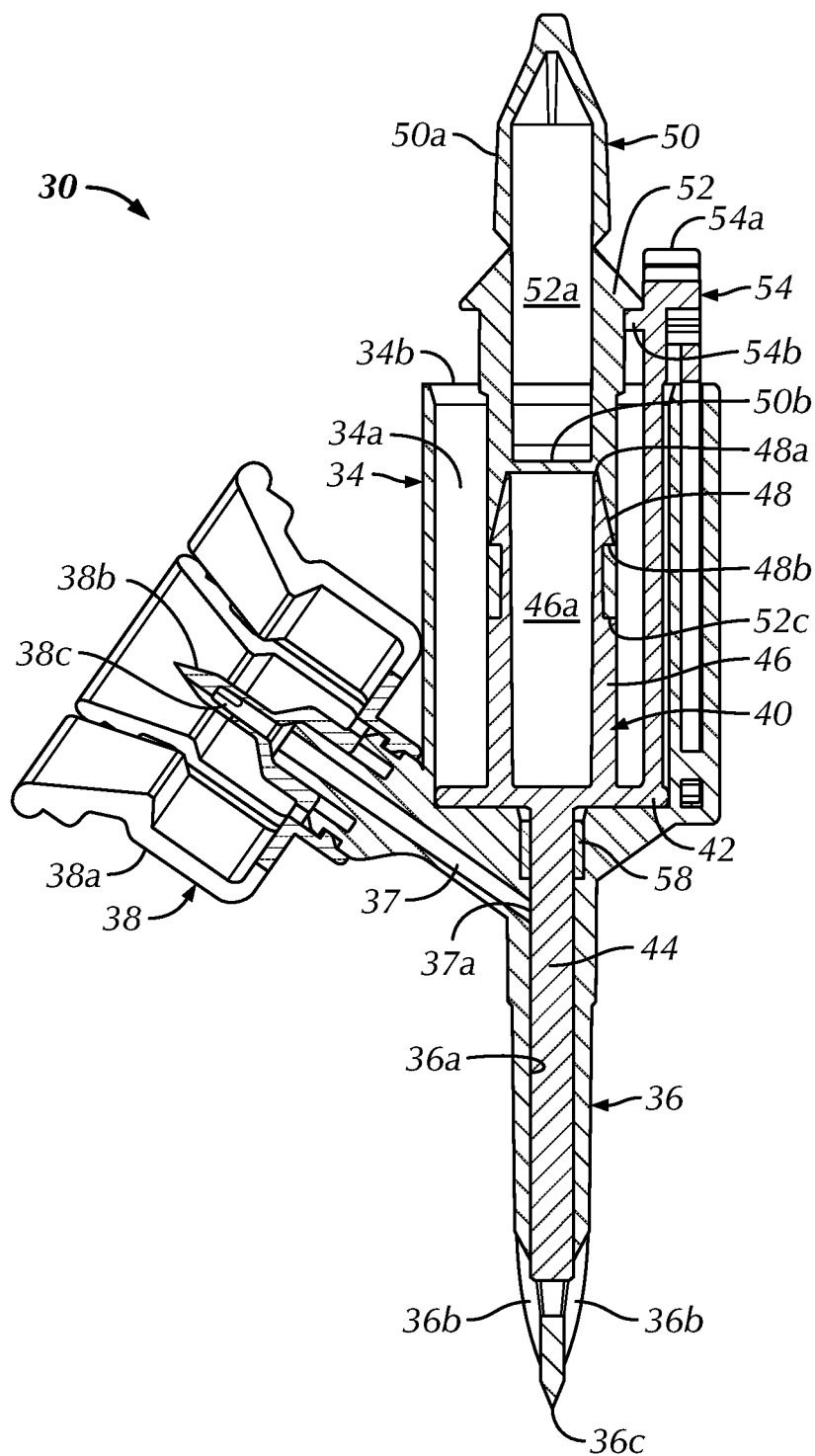
FIG. 5B is a cross-sectional elevational view of the liquid transfer device of FIG. 5A, taken along sectional line 5B-5B of FIG. 5A.
Figure 5C:
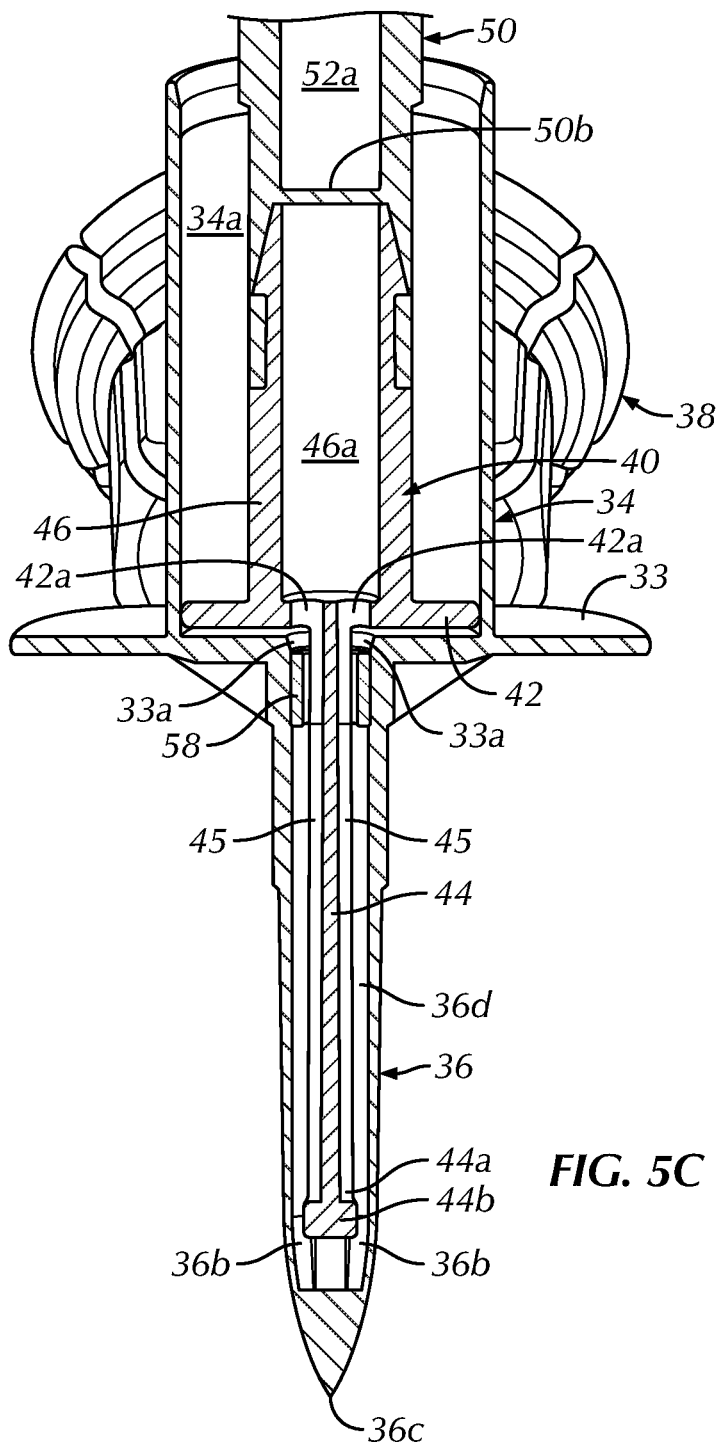
FIG. 5C is a partial, cross-sectional elevational view of the liquid transfer device of FIG. 5A, taken along sectional line 5C-5C of FIG. 5A.

Turning to the relationship between the IV spike 36 and the plunger 40, the IV spike lumen 36a defines a generally circular cross-section, having at least one elongate, grooved channel 36d in the periphery thereof (FIG. 3E), extending from proximate the flange 33 to the distal apertures 36b (see FIGS. 3C, 4C, 5C). In the illustrated embodiment, the grooved channel is substantially semi-circular/moon-shaped in cross-section, but the disclosure is not so limited. The plunger rod 44 of the plunger 40, slidable within the IV spike lumen 36a, defines a generally complementary cross-section to the cross-section of the IV spike lumen 36a and includes a corresponding at least one elongate, grooved channel 44a in the periphery thereof, extending from the piston face 42 to a distal head 44b of the plunger rod 44 and facing/opposing the grooved channel 36d of the IV spike lumen 36a (see FIGS. 3C, 3E, 4C, 5C). The opposing grooved channels 36d and 44a define a cross-sectionally enclosed fluid-flow pathway 45 therebetween. Therefore, the plunger rod 44 substantially sealingly engages the periphery of the IV spike lumen 36a, except for the fluid-flow pathway 45. In the illustrated embodiment, the IV spike lumen 36a includes two diametrically opposed grooved channels 36d and the plunger rod 44 includes two diametrically opposed grooved channels 44a, thereby defining two diametrically opposed fluid-flow pathways 45 between the plunger rod 44 and the IV spike lumen 36a, but the disclosure is not so limited (to the number of fluid-flow pathways 45 or to being diametrically opposed). Aperture(s) 33a in the flange 33, aligned with the fluid-flow pathway(s) 45, fluidly communicate the pathway(s) 45 with the barrel chamber 34a. The distal head 44b defines a fully circular (groove-less) cross-section. As shown in FIGS. 3C, 4C, the fluid-flow pathway(s) 45 are not aligned with the vial adapter lumen 37. Thus, the plunger rod 44 may seal off the opening 37a of the vial adapter lumen 37 from fluid communication with the IV spike lumen 36a, as will be described in further detail below. As should be understood by those of ordinary skill in the art, the IV spike lumen 36a may define a different shape in cross-section and the plunger rod 44 may also define a different shape in cross-section, so long as the plunger rod 44 substantially sealingly engages the periphery of the IV spike lumen 36a, except for the fluid-flow pathway(s) 45, and the fluid-flow pathway(s) 45 are not aligned with the vial adapter lumen 37.

As shown in FIGS. 2, 3A, 3B, 3D, 4A, 4B, 4B, 5A, 5B and 5D, the liquid transfer device 30 includes a plunger handle assembly 54 fixedly attached to the plunger 40. In the illustrated embodiment, the plunger handle assembly 54 extends proximally upright from the top side of the piston face 42, having a handle 54a at a free, proximal end thereof. In one embodiment, the plunger handle assembly 54 is integrally, i.e., monolithically, formed with the piston face 42, but the disclosure is not so limited. In the illustrated embodiment, the plunger handle assembly 54 extends substantially parallel to the plunger tube 46 and the IV port 50, but the disclosure is not so limited. Optionally, the plunger handle assembly 54 includes a support 54b laterally extending from the handle 54a (or proximate the handle 54a), and into engagement with the IV port 54, e.g., snap fit onto or cradle the elongate member 52, to provide additional support for the plunger handle assembly 54.

Figure 3D:
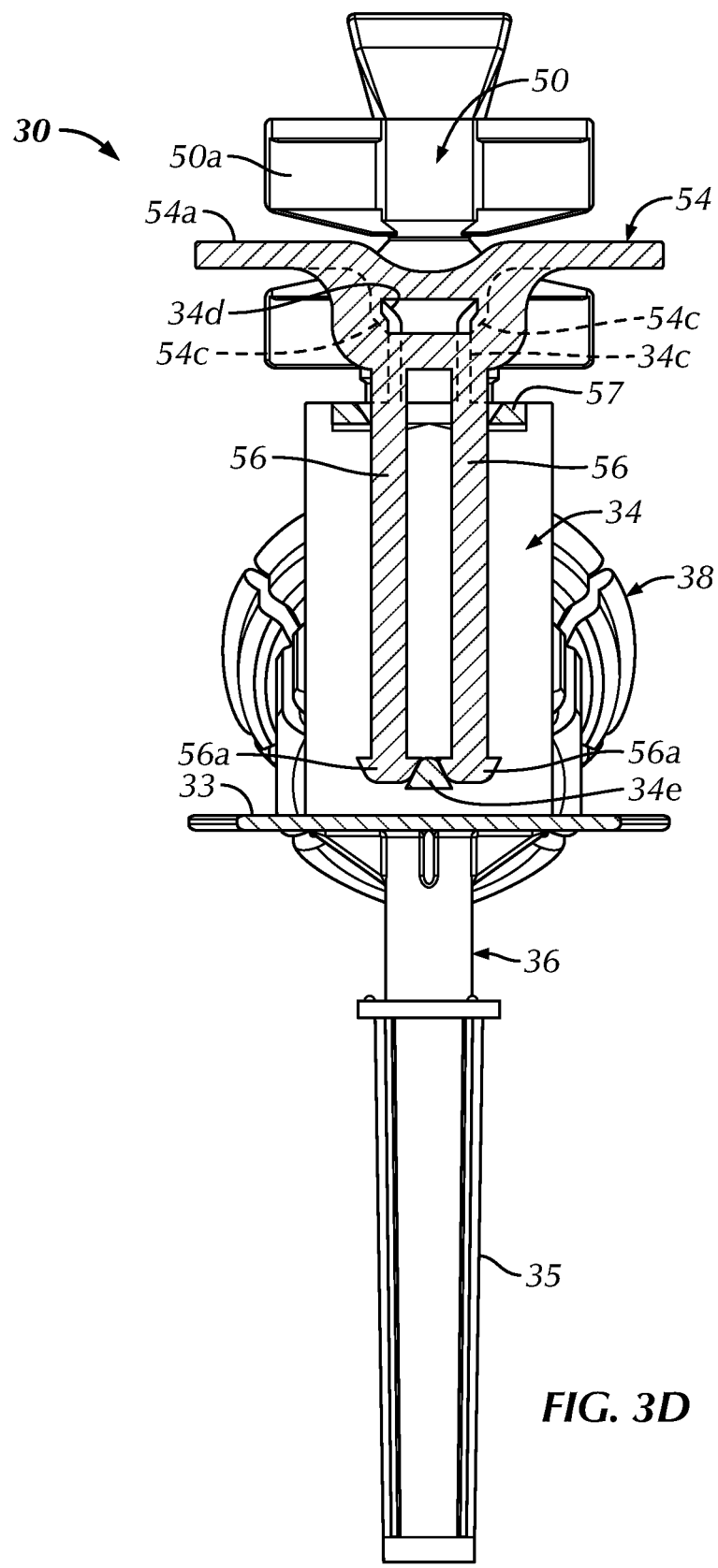
FIG. 3D is a cross-sectional elevational view of the liquid transfer device of FIG. 3A, taken along sectional line 3D-3D of FIG. 3A.
Figure 3E:
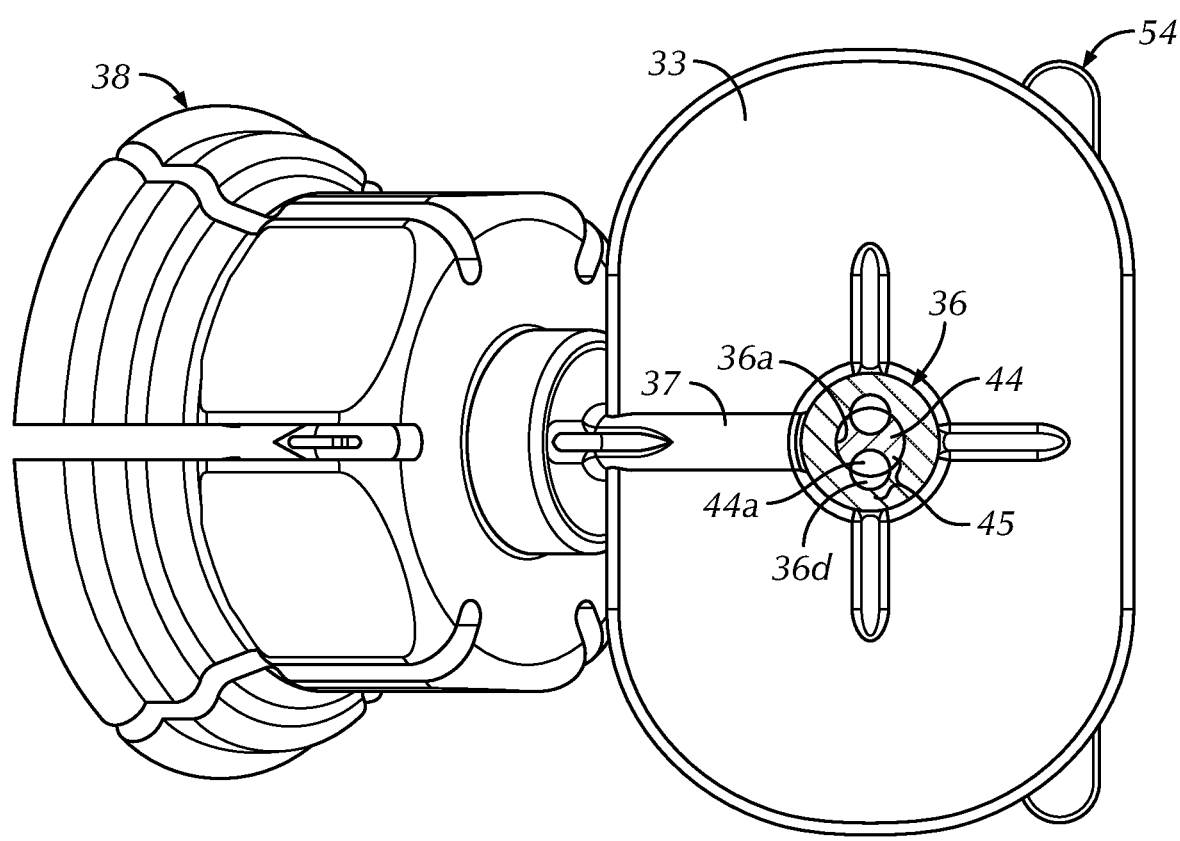
FIG. 3E is a cross-sectional, bottom plan view of the liquid transfer device of FIG. 3A, taken along sectional line 3E-3E of FIG. 3A.
Figure 4D:
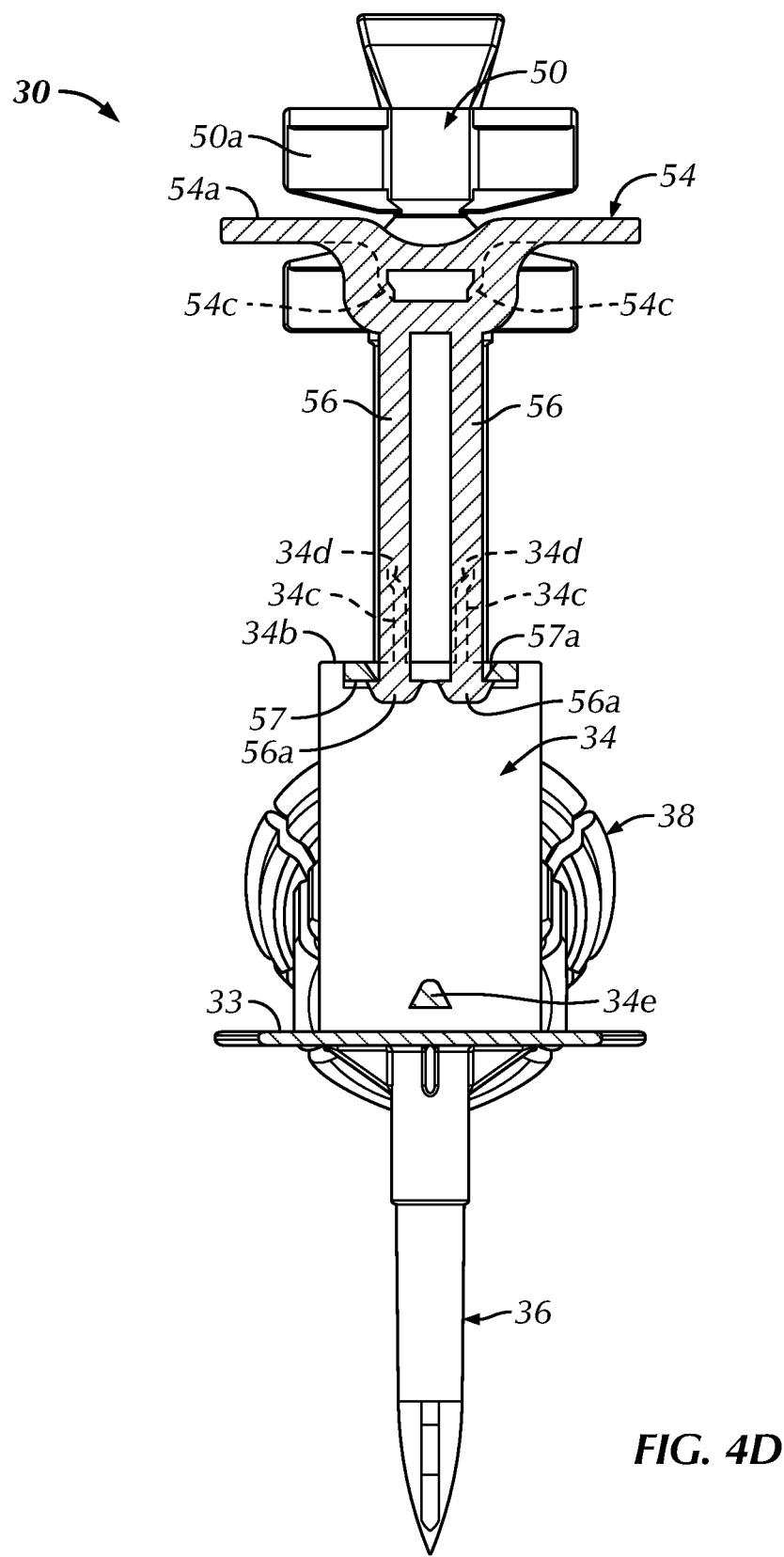
FIG. 4D is a cross-sectional elevational view of the liquid transfer device of FIG. 4A, taken along sectional line 4D-4D of FIG. 4A.
Figure 5D:
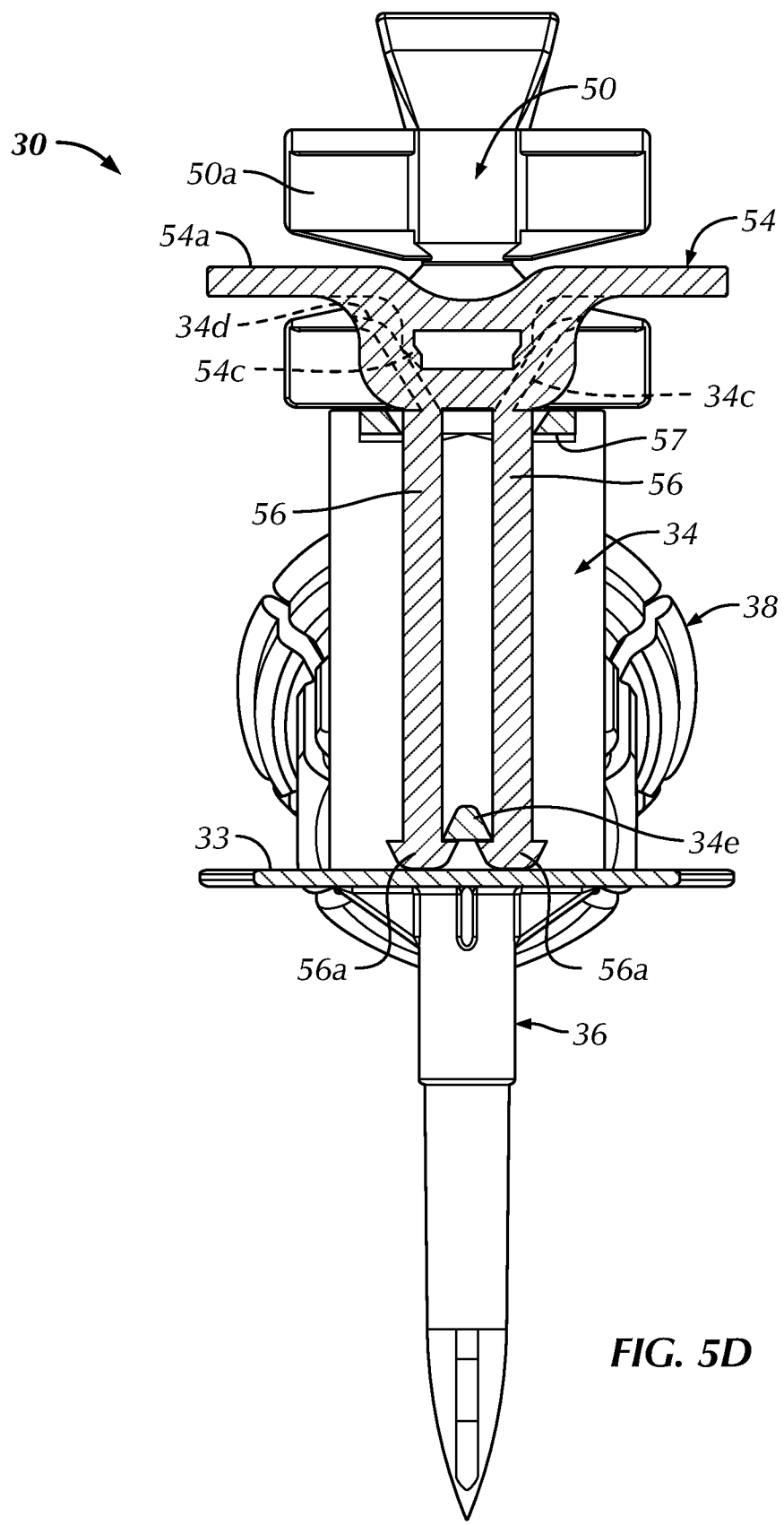
FIG. 5D is a cross-sectional elevational view of the liquid transfer device of FIG. 5A, taken along sectional line 5D-5D of FIG. 5A.

As shown best in FIGS. 3D, 4D, and 5D, the plunger handle assembly 54 includes a pair of parallelly extending arms 56 projecting downwardly (distally) from the plunger handle 54a (outside of the barrel 34) and terminate in respective flanged ends 56a. The barrel 34 includes a pair of deflectable fingers 34c projecting upright from the open proximal end 34b thereof, and into engagement with the handle 54a. The barrel 34 further includes a stop tab 34e positioned on the exterior wall thereof, between the flanged ends 56a of the arms 56.

In use, the liquid transfer device 30 is delivered to a user in a partially-locked, pre-mixing configuration, as shown in FIGS. 3A-3D. In the pre-mixing configuration, the plunger 40 is depressed within the barrel 34 until the piston face 42 is substantially at the same elevation of the stop tab 34e. In this configuration, the plunger 40 is close to bottoming out within the barrel 34, reducing the footprint of the liquid transfer device 30 during delivery. In the partially-locked, pre-mixing configuration, the fingers 34c are positioned in an undeflected orientation and abut an underside of the handle 54a, preventing further depression (i.e., full depression) of the handle 54a and the plunger 40. The fingers 34c include laterally outwardly directly hooked terminal ends 34d, which engage corresponding downwardly and laterally inwardly directed hooks 54c projecting from an underside of the handle 54a (FIG. 3D). The engagement between the hooks 54c and the hooked terminal ends 34d stabilizes (partially-locks) the plunger 40 in the pre-mixing configuration. In the partially-locked, pre-mixing configuration, the flanged terminal ends of the arms 56 abut the stop tab 34e, positioned therebetween.

In the partially-locked, pre-mixing configuration, the liquid transfer device 30 may be coupled to an infusion liquid bag 10 via the IV spike 36 (as previously described) and with a vial 20 via the vial adapter 38 (as previously described). Thereafter, as shown in FIGS. 4A-4D, the user withdraws the plunger 40 (in a direction away from the infusion liquid bag 10) via the handle 54. Withdrawal of the plunger 40 is required to be performed with sufficient force such that the hooks 54c deflect the fingers 34c laterally inwardly (toward one another) during withdrawal and slidably disengage therefrom. The plunger 40 is fully withdrawn upon reaching a stop mechanism, which prevents inadvertent detachment of the plunger 40 from the barrel 34. In the illustrated embodiment, the stop mechanism includes a wall 57 laterally extending from the barrel 34, adjacent the open end 34b thereof (see FIGS. 3A, 4A, 5A). As shown best in FIG. 4D, the wall 57 includes an opening 57a dimensioned to permit sliding of the pair of parallelly extending arms 56 together therethrough, and to block the passage of the flanged terminal ends 56a therethrough. Therefore, the plunger 40 is stopped from further withdrawal upon contact of the flanged terminal ends 56a with the underside of the wall 57. As should be understood, however, the stop mechanism may take other forms currently known, or that later become known, capable of performing the same function of the stop mechanism described herein.

Withdrawal of the plunger 40, with the IV spike apertures 36b immersed in the infusion liquid within the bag 10, pulls fluid from the bag 10, through the apertures 36b, through the fluid-flow pathway(s) 45, i.e., between opposing grooved channels 36d and 44a, and into the barrel chamber 34a via the aperture(s) 33a. As should be understood by those of ordinary skill in the art, withdrawal of the plunger 40 creates a vacuum in the barrel chamber 34a, resulting in a pressure difference relative to the infusion liquid bag 10, thereby pulling the fluid into the barrel chamber 34a. As shown best in FIGS. 3C, 4C and 5C, a bushing 58 is positioned within the IV spike lumen 36a, adjacent the underside of the flange 33. The external periphery of the bushing 58 is configured (sized, shaped and dimensioned) to seal with the periphery of the IV spike lumen 36a. The internal aperture of the bushing 58 is configured (sized, shaped and dimensioned) to permit sliding of the plunger rod 44 therethrough and to engage the distal head 44b of the plunger rod 44, via a transition fit or a press fit, when the plunger 40 is fully withdrawn. The length of the barrel 34, the IV spike 36, the plunger rod 44 and the bushing 58, in combination with the position of the stop mechanism, are configured such that full withdrawal of the plunger 40 coincides with engagement of the distal head 44b of the plunger rod 44 with the bushing 58 (FIG. 4C), thereby sealing off the elongate, grooved channel(s) 44a of the plunger rod 44 from the elongate, grooved channel(s) 36d of the IV spike lumen 36a, and, in turn, sealing the infusion liquid within the barrel chamber 34a.

As previously described, the fluid-flow pathway(s) 45 is not aligned with the vial adapter lumen 37 and the plunger rod 44 seals off the opening 37a of the vial adapter lumen 37 from fluid communication with the IV spike lumen 36a during plunger 40 withdrawal, such that fluid may substantially only flow into the barrel chamber 34a. Upon reaching the fully withdrawn position of the plunger 40, the liquid transfer device 30 is in a ready-to-mix position. In the ready-to-mix position, as shown in FIGS. 4B and 4C, the distal head 44b of the plunger rod 44 is positional proximal to the opening 37a of the vial adapter lumen 37. That is, upon reaching the fully withdrawn position, the plunger rod 44 clears the vial adapter lumen opening 37a, thereby fluidly communicating the vial adapter lumen 37 with the IV spike lumen 36a, while sealing off the reservoir barrel 34a.

In the ready-to-mix position, the contents within the infusion liquid bag 10 are fluidly connected and mixable/combinable with the contents within the vial 20, via the fluidly connected vial adapter lumen 37 and the IV spike lumen 36a. Mixing and/or combining the contents within the infusion liquid bag 10 with the contents within the vial 20 (to create a medicated infusion liquid) is then performed. In the case that the vial 20 contains a lyophilized powder drug, the drug can be reconstituted by squeezing on the infusion liquid bag 10 to force liquid from the infusion liquid bag 10 into the vial 20.

After mixing/combining the contents within the infusion liquid bag 10 and the vial 20 and orienting the liquid transfer device 30 such that the combined liquid flows into the infusion liquid bag 10, the plunger 40 is fully depressed into a fully-locked, post-mixing configuration (as shown in FIGS. 5A-5D). Depressing the plunger 40 (via the handle 54a) disengages the distal head 44b of the plunger rod 44 from the bushing 58, re-connecting the elongate, grooved channel(s) 44a of the plunger rod 44 with the elongate, grooved channel(s) 36d of the IV spike lumen 36a to fluidly communicate the barrel chamber 34a with the IV spike lumen 36a and once again sealing off the vial adapter lumen opening 37a from fluid communication with the IV spike lumen 36a. The piston face 42 pushes out the fluid within the barrel chamber 34a, through the IV spike lumen 36a and out the distal apertures 36b. Advantageously, therefore, after mixing the contents within the infusion liquid bag 10 and the vial 20, substantially any remaining unmixed medicament liquid additive or un-reconstituted lyophilized powder drug within the vial adapter lumen 37 is sealed off, and substantially any remaining unmixed medicament liquid additive or un-reconstituted lyophilized powder drug within the IV spike lumen 36a is flushed out of the lumen 36a and mixed into the infusion liquid bag 10 by the fluid within the barrel chamber 34a.

During depression of the plunger 40, the laterally inwardly directed hooks 54c projecting from an underside of the handle 54a re-engage the outwardly directly hooked terminal ends 34d of the fingers 34c and deflect the fingers 34c laterally outwardly (away from one another) (see FIG. 5D), thereby preventing the fingers 34c from abutting the underside of the handle 54a and enabling full depression of the plunger 40. When the plunger 40 is fully depressed (see FIGS. 5B, 5C), the piston face 42 bottoms out within the barrel chamber 34a, and the plunger handle assembly 54 fully locks into the post-mixing configuration via a locking mechanism. In the illustrated embodiment, the locking mechanism is activated through contact between the flanged ends 56a of the arms 56 and the intervening stop tab 34e as the plunger 40 is depressed. The flanged ends 56a and the stop tab 34e are configured such that the stop tab 34e deflects the arms 56 laterally away from one another to surpass the stop tab 34e (during plunger 40 depression) and, thereafter, the flanged ends 56a snap back around the stop tab 34e (FIG. 5D) and hook onto the underside thereof. Once the flanged ends 56a hooks onto the underside of the stop tab 34e, the plunger 40 is fully locked, i.e., the plunger 40 may not be withdrawn without causing damage to the stop tab 34e, the arms 56 or another component of the liquid transfer device 30. As should be understood by those of ordinary skill in the art, however, other locking mechanisms may be employed that are currently known, or that later become known, performing the function of the locking mechanism described herein.

Figure 1D:
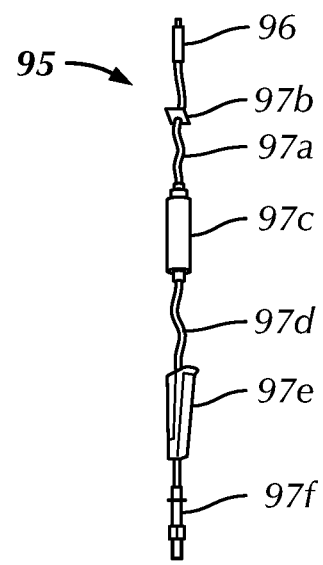
FIG. 1D is a front elevational view of an infusion set usable with the liquid transfer device according to the present disclosure.

As shown best in FIG. 5C, the piston face 42 includes at least one aperture 42a aligned with the aperture(s) 33a in the flange 33. Thus, in the fully-locked, post-mixing configuration of the liquid transfer device 30, the plunger lumen 46a is in fluid communication with the IV spike lumen 36a, via the aperture(s) 42a and the aperture(s) 33a (with the vial adapter lumen 37 sealed off, as previously described). In the post-mixing configuration, the twist-off member 50a is removed, providing access to the internal lumen 52a. Thereafter, an IV spike 96 of an infusion set 95 (FIG. 1D) is sealingly inserted into the internal lumen 52a and penetrates the septum 50b, thereby fluidly connecting the IV spike 96 with any remainder of the internal lumen 52a beyond the septum 50a, and, in turn, with the plunger lumen 46a and the IV spike lumen 36a for administration of the medicated infusion liquid to a patient. Conventionally, an infusion set 30 additionally includes first tubing 97a, a clamp 97b, a drip chamber 97c, second tubing 97d, a roller clamp 97e, and a male Luer connector 97f for controlling fluid administration to a patient.

It will be appreciated by those skilled in the art that changes could be made to the embodiments described above without departing from the broad inventive concepts thereof. For example, the trifurcated connector body 32 may include a vial adapter at the second end thereof (for use with an infusion liquid bottle 18) and/or a normally closed (NC) needleless additive port (not shown) at the third end thereof (enabling selection of use with a syringe 22 or with a vial 20), as described in U.S. Pat. No. 8,551,067, entitled, "Needleless Additive Control Valve," the entire contents of which are incorporated by reference herein. As another example, the vial adapter 38 can be replaced by a manually operated stop cock, and the like. It is understood, therefore, that this invention is not limited to the particular embodiments disclosed, but it is intended to cover modifications within the spirit and scope of the present disclosure, as set forth in the appended claims.

I claim:

1. A liquid transfer device configured for use with each of an infusion liquid container having an intravenous (IV) port, a vial sealed by a vial stopper, and an infusion set including an IV spike for sealing insertion into an IV port, the liquid transfer device comprising:
a trifurcated connector body defining a barrel at a first end thereof, an IV spike at a second end thereof and a vial adapter lumen at a third end thereof,
the barrel defining an internal chamber having an open proximal end,
the IV spike defining an internal IV spike lumen having a distally located first aperture, and the IV spike being configured to sealingly insert into the IV port of the infusion liquid container, and the vial adapter lumen branching off of the IV spike lumen;

a vial adapter secured to the vial adapter lumen and configured to mount onto the vial, the vial adapter including a cannula fluidly connected with the vial adapter lumen and configured to puncture the vial stopper upon mounting of the vial adapter onto the vial for flow communication therewith, a plunger in slidable engagement with the internal chamber of barrel via the open proximal end thereof, the plunger comprising:
- a piston face transversely oriented relative to, and in sealing engagement with, the barrel,
- a tube projecting proximally from the piston face and terminating in an IV port configured to sealingly receive the IV spike of the infusion set, the tube defining an internal plunger lumen therein, and
- a plunger rod projecting distally from the piston face and into the IV spike lumen, the plunger rod and the IV spike lumen defining a fluid-flow pathway therebetween, the fluid-flow pathway being sealed off from the vial adapter lumen; and a second aperture interposed between a distal end of the internal chamber of the barrel and a proximal end of the IV spike lumen, and aligned with the fluid-flow pathway, to fluidly connect the fluid-flow pathway with the internal chamber of the barrel;

wherein:
- in an advanced position of the plunger, the plunger rod seals off the vial adapter lumen from fluid communication with the IV spike lumen and the internal chamber of the barrel is in fluid communication with the IV spike lumen and the first aperture of the IV spike via the fluid-flow pathway and the second aperture, and
- in a retracted position of the plunger, the plunger rod seals off the internal chamber of the barrel from fluid communication with the IV spike lumen and the first aperture of the IV spike, and the vial adapter lumen is fluidly communicated with the IV spike lumen and the first aperture of the IV spike.

2. The liquid transfer device of claim 1,
wherein the IV spike lumen includes at least one elongate grooved channel in a periphery of the IV spike lumen, extending from proximate the barrel to the first aperture, and the plunger rod includes a corresponding and opposing at least one elongate grooved channel in a periphery of the plunger rod, extending from the piston face to a distal head of the plunger rod, the at least one elongate grooved channel in the periphery of the IV spike lumen and the corresponding and opposing at least one elongate grooved channel in the periphery of the plunger rod forming the fluid-flow pathway.

3. The liquid transfer device of claim 2,
wherein the plunger rod defines a complementary cross-section to a cross-section of the IV spike lumen, other than along the at least one elongate grooved channel, such that the plunger rod substantially sealingly engages the periphery of the IV spike lumen except along the fluid-flow pathway.

4. The liquid transfer device of claim 2,
wherein the distal head of the plunger rod is positioned proximal of the vial adapter lumen in the retracted position of the plunger, thereby clearing the vial adapter lumen for fluid communication with the IV spike lumen and the first aperture of the IV spike.

5. The liquid transfer device of claim 2,
further comprising a bushing positioned within the IV spike lumen adjacent an underside of the second opening, an external periphery of the bushing being configured to seal with the periphery of the IV spike lumen and an internal aperture of the bushing being configured to permit sliding of the plunger rod therethrough and to sealing engage the distal head of the plunger rod in the retracted position thereof, thereby sealing off the internal chamber of the barrel from fluid communication with the IV spike lumen and the first aperture of the IV spike.

6. The liquid transfer device of claim 2,
wherein the distal head of the plunger rod defines a grove-less cross-section.

7. The liquid transfer device of claim 1,
wherein the piston face defines a third aperture at a distal end of the internal plunger lumen, the third aperture being aligned with the second aperture, wherein:
- in the advanced position of the plunger, the internal plunger lumen is also in fluid communication with the IV spike lumen and the first aperture of the IV spike via the third aperture, the second aperture and the fluid-flow pathway, and
- in the retracted position of the plunger, the plunger rod also seals off the internal plunger lumen from fluid communication with the IV spike lumen and the first aperture of the IV spike.

8. The liquid transfer device of claim 1,
wherein the fluid-flow pathway is angularly offset from the vial adapter lumen.

9. The liquid transfer device of claim 1,
wherein the IV spike is co-directional with the barrel.

10. The liquid transfer device of claim 1,
further comprising a plunger handle assembly attached to the plunger, for advancing and retracting the plunger, the plunger handle assembly being positioned outside of the barrel.

11. The liquid transfer device of claim 10,
wherein the plunger handle assembly comprises a handle and a pair of arms projecting distally from the handle, the arms terminating in respective flanged ends, and
wherein the barrel includes a stop tab positioned on an exterior wall of the barrel, aligned between the flanged ends of the arms, and a pair of deflectable fingers projecting proximally from the open proximal end of the barrel.

12. The liquid transfer device of claim 11,
wherein the plunger is distally depressed within the internal chamber of the barrel in a first configuration of the liquid transfer device, wherein the pair of deflectable fingers engage an underside of the handle and prevent further depression of the plunger and the pair of deflectable fingers are prevented from deflecting by respective distally projecting hooks of the handle.

13. The liquid transfer device of claim 12,
wherein the barrel further includes a stop mechanism extending from the exterior wall of the barrel, and wherein the plunger is proximally retractable within the internal chamber of the barrel into a second configuration of the liquid transfer device, the second configuration of the liquid transfer device corresponding generally to a maximum retraction of the plunger within the internal chamber of the barrel, wherein the flanged ends of the arms of the plunger handle assembly engage the stop mechanism.

14. The liquid transfer device of claim 13, wherein the pair of deflectable fingers of the barrel are disengaged from the distally projecting hooks of the handle in the second configuration of the liquid transfer device, the pair of deflectable fingers being deflected away from the underside of the handle during subsequent distal depression of the plunger, thereby permitting distal depression of the plunger within the internal chamber of the barrel beyond the first configuration of the liquid transfer device and into a third configuration of the liquid transfer device, wherein the flanged ends of the arms of the plunger handle assembly surpass, and snap back onto, the stop tab, thereby locking the liquid transfer device into the third configuration, wherein the third configuration of the liquid transfer device corresponds generally to a maximum depression of the plunger within the internal chamber of the barrel.

15. A method of mixing a medicament additive contained within a vial and sealed by a vial stopper with an infusion liquid contained within an infusion liquid container, with a liquid transfer device, to form a medicated infusion liquid, the method comprising:
   sealingly inserting an IV spike of the liquid transfer device into an IV port of the infusion liquid container, the liquid transfer device comprising:
      a trifurcated connector body defining a barrel at a first end thereof, the IV spike at a second end thereof and a vial adapter lumen at a third end thereof,
         the barrel defining an internal chamber having an open proximal end,
         the IV spike defining an internal IV spike lumen having a distally located first aperture, and
         the vial adapter lumen branching off of the IV spike lumen;
      a vial adapter secured to the vial adapter lumen, the vial adapter including a cannula fluidly connected with the vial adapter lumen;
      a plunger in slidable engagement with the internal chamber of the barrel via the open proximal end thereof, the plunger comprising:
         a piston face transversely oriented relative to, and in sealing engagement with the barrel,
         a tube projecting proximally from the piston face and terminating in an IV port, the tube defining an internal plunger lumen therein, and
         a plunger rod projecting distally from the piston face and into the IV spike lumen, the plunger rod and the IV spike lumen defining a fluid-flow pathway therebetween, the fluid-flow pathway being sealed off from the vial adapter lumen; and
      a second aperture interposed between a distal end of the internal chamber of the barrel and a proximal end of the IV spike lumen, and aligned with the fluid-flow pathway to fluidly connect the fluid-flow pathway with the internal chamber of the barrel;
      wherein:
         in an advanced position of the plunger, the plunger rod seals off the vial adapter lumen from fluid communication with the IV spike lumen and the internal chamber of the barrel is in fluid communication with the IV spike lumen and the first aperture of the IV spike via the fluid-flow pathway and the second aperture, and
         in a retracted position of the plunger, the plunger rod seals off the internal chamber of the barrel from fluid communication with the IV spike lumen and the first aperture of the IV spike, and the vial adapter lumen is fluidly communicated with the IV spike lumen and the first aperture of the IV spike;
   mounting the vial adapter onto the vial and puncturing the vial stopper for flow communication between the vial and the vial adapter lumen;
   withdrawing the plunger proximally through the internal chamber of the barrel, from the advanced position thereof toward the retracted position thereof, and, in turn, pulling a volume of the infusion liquid into the internal chamber of the barrel;
   sealing off the internal chamber of the barrel from fluid communication with the IV spike lumen and the first aperture of the IV spike upon reaching the retracted position of the plunger;
   combining the medicament additive contained within the vial with the infusion liquid within the infusion liquid container via fluid communication between the vial adapter lumen, the IV spike lumen and the first aperture of the IV spike when the plunger is in the retracted position, to form a medicated infusion liquid; and
   depressing the plunger distally through the internal chamber to re-seal the vial adapter lumen from fluid communication with the IV spike lumen, re-communicate the internal chamber of the barrel with the IV spike lumen and the first aperture of the IV spike, and push out the volume of the infusion liquid within the internal chamber through the IV spike lumen, out of the first aperture and into the infusion liquid container.

16. The method of claim 15, wherein the liquid transfer device further comprises a plunger handle assembly attached to the plunger and positioned outside of the barrel, and wherein the withdrawing step comprises withdrawing via the plunger handle assembly, and the depressing step comprises depressing via the plunger handle assembly.

17. The method of claim 16, wherein the plunger handle assembly comprises a handle and a pair of arms projecting distally from the handle, the pair of arms terminating in respective flanged ends, and the barrel includes a stop tab positioned on an exterior wall of the barrel, aligned between the flanged ends of the pair of arms, a stop mechanism extending from the exterior wall of the barrel and a pair of deflectable fingers projecting proximally from the open proximal end of the barrel, wherein the withdrawing step further comprises:
   withdrawing the plunger proximally through the internal chamber of the barrel until the flanged ends of the pair of arms of the plunger handle assembly engage the stop mechanism, corresponding to a maximum retraction of the plunger within the internal chamber of the barrel.

18. The method of claim 17, further comprising the step of:
   locking the plunger in place relative to the barrel, after the depressing step, to prevent subsequent movement thereof.

19. The method of claim 18, wherein the locking step comprises depressing the plunger distally until the flanged ends of the pair of arms of the plunger handle assembly surpass, and snap back onto, the stop tab.

20. The method of claim 15,
wherein the piston face defines a third aperture at a distal end of the internal plunger lumen, the third aperture being aligned with the second aperture and fluidly connecting the internal plunger lumen with the fluid-flow pathway, the method further comprising the step of:

sealingly inserting an IV spike of an infusion set into the IV port of the plunger after the depressing step, and, in turn, fluidly communicating the infusion set with the medicated infusion liquid within the infusion liquid container, via the first aperture of the IV spike, the fluid-flow pathway, the second aperture, the third aperture and the internal plunger lumen.

* * * * *